US011607554B2

(12) United States Patent
Finch et al.

(10) Patent No.: US 11,607,554 B2
(45) Date of Patent: *Mar. 21, 2023

(54) WEARABLE CARDIOVERTER DEFIBRILLATION (WCD) SYSTEM WITH PROXIMATE PROGRAMMING DEVICE WHICH STORES ECG DATA THAT THE WCD SYSTEM NORMALLY DISCARDS

(71) Applicant: WEST AFFUM HOLDINGS DAC, Dublin (IE)

(72) Inventors: David Peter Finch, Bothell, WA (US); Zoie Engman, Kirkland, WA (US); Steven E. Sjoquist, Lynnwood, WA (US); Angela M. Stewart, Granite Falls, WA (US); Pamela Breske, Newcastle, WA (US); Jonathan Paul Niegowski, Issaquah, WA (US); Laura Marie Gustavson, Redmond, WA (US)

(73) Assignee: West Affum Holdings DAC, Dublin (IE)

( * ) Notice: Subject to any disclaimer, the term of this patent is extended or adjusted under 35 U.S.C. 154(b) by 320 days.

This patent is subject to a terminal disclaimer.

(21) Appl. No.: 16/936,285

(22) Filed: Jul. 22, 2020

(65) Prior Publication Data
US 2020/0346026 A1    Nov. 5, 2020

Related U.S. Application Data

(63) Continuation of application No. 16/010,254, filed on Jun. 15, 2018, now Pat. No. 10,737,104.
(Continued)

(51) Int. Cl.
*A61N 1/39*    (2006.01)
*A61N 1/04*    (2006.01)
(Continued)

(52) U.S. Cl.
CPC .............. *A61N 1/3904* (2017.08); *A61B 5/25* (2021.01); *A61B 5/332* (2021.01); *A61B 5/349* (2021.01);
(Continued)

(58) Field of Classification Search
CPC ........................ A61N 1/3904; A61B 5/0404
(Continued)

(56) References Cited

U.S. PATENT DOCUMENTS

| 3,724,355 A | 4/1973 | Unger |
| 4,583,524 A | 4/1986 | Hutchins |

(Continued)

FOREIGN PATENT DOCUMENTS

| WO | 9839061 A2 | 9/1998 |
| WO | 1998039061 A2 | 9/1998 |
| WO | 2012064604 A1 | 5/2012 |

OTHER PUBLICATIONS

Klein, H. U., Goldenberg I., & Moss, A. J., Risk Stratification for Implantable Cardioverter Defibrillator Therapy The Role of the Wearable Cardioverter-Defibrillator, Clinical update, European Heart Jounal, May 31, 2013, pp. 1-14, doi:10.1093/eurheartj/eht167, European Society of Cardiology.
(Continued)

*Primary Examiner* — Nadia A Mahmood
(74) *Attorney, Agent, or Firm* — Christensen O'Connor Johnson Kindness PLLC

(57) ABSTRACT

In embodiments, a wearable medical system (WMS) for an ambulatory patient, which can be a wearable cardioverter defibrillator (WCD) system, analyzes the patient's ECG signal to generate a detection outcome. The WMS also has an ambulatory user interface that outputs a human-visible indication. A programming device, such as a PC, a tablet, etc., establishes a communication link with the WMS during
(Continued)

an in-person session with the patient. The programming device may include a programming screen that reproduces the human-visible indication in real time. An advantage can be that the person programming the WMS need not strain to look also at the ambulatory user interface at the time they are looking at the programming device. Another advantage can be that the patient will recognize that he or she is better protected, and have their confidence in the WMS increased, and therefore better comply with wearing the WMS as required.

20 Claims, 27 Drawing Sheets

Related U.S. Application Data

(60) Provisional application No. 62/538,131, filed on Jul. 28, 2017.

(51) Int. Cl.
| | | |
|---|---|---|
| *A61B 5/00* | | (2006.01) |
| *A61B 5/25* | | (2021.01) |
| *A61B 5/332* | | (2021.01) |
| *A61B 5/349* | | (2021.01) |

(52) U.S. Cl.
CPC ............ *A61B 5/6805* (2013.01); *A61B 5/742* (2013.01); *A61B 5/747* (2013.01); *A61B 5/7475* (2013.01); *A61N 1/046* (2013.01)

(58) Field of Classification Search
USPC .......................................................... 607/142
See application file for complete search history.

(56) References Cited

U.S. PATENT DOCUMENTS

| | | | |
|---|---|---|---|
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bomn et al. |
| 5,353,793 A | 10/1994 | Bomn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lysler |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 10/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,454,219 B2 | 9/2016 | Volpe et al. |
| 9,592,403 B2 | 3/2017 | Sullivan |
| 9,878,171 B2 | 1/2018 | Kaib |
| 9,901,741 B2 | 2/2018 | Chapman et al. |
| 10,016,613 B2 | 7/2018 | Kavounas |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Burtonil et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee et al. |
| 2016/0283900 A1 | 9/2016 | Johnson et al. |
| 2016/0331986 A1 | 11/2016 | Piha et al. |
| 2017/0319862 A1 | 11/2017 | Foshee, Jr. et al. |
| 2017/0367591 A1 | 12/2017 | Jorgenseon |
| 2018/0116537 A1 | 5/2018 | Sullivan et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2019/0030352 A1 | 1/2019 | Sullivan et al. |
| 2019/0076666 A1 | 3/2019 | Medema |

(56) References Cited

U.S. PATENT DOCUMENTS

OTHER PUBLICATIONS

Lifecor LifeVest System Model WCD 3100 Operator's Manual, 2006, PN 20B0040 Rev FI, Zoll Lifecor Corporation, Pittsburgh, PA.
Heartstart MRx and XL AED Algorithm—Application Note, Jul. 2001, Edition 2 Phillips Healthcare, USA.
Zoll LifeVest Model 4000 Patient Manual PN 20B0047 Rev B, (C) 2009-2012.
Pagan-Carlo, et al., "Encircling Overlapping Multipulse Shock Waveforms for Transthoracic Defibrillation," JACC Journals, Dec. 1998, vol. 32 Issue 7, p. 2065-2071.
The LifeVest Network/Patient Data Management System, Zoll, 2015, 2000503 Rev A.

| COMPONENT | SAMPLE USER(S) | COMPONENT EXAMPLES |
|---|---|---|
| MEDICAL DEVICE(S) | * PATIENT<br>* PHYSICIAN / HEALTH CARE PROVIDERS<br>* FIRST RESPONDERS<br>* BYSTANDERS<br>* CARE GIVERS<br>* MANUF. REP.S* | * WCD ELECTRONICS MODULE<br>* WCD CHARGER<br>* WCD ASSISTANT<br>* WCD TABLET<br>* RELATED DEVICES (E.G. BP MONITOR, INSULIN PUMP, CPAP, ICD, AED, SALINE PUMP, ETC.) |
| INTERFACING COMPONENT(S) | * PATIENTS<br>* PHYSICIAN / HEALTH CARE PROVIDERS<br>* FIRST RESPONDERS<br>* BYSTANDERS<br>* CARE GIVERS<br>* MANUF. REP.S* | * WCD ASSISTANT<br>* WCD TABLET<br>* RELATED DEVICES (E.G. BP MONITOR, INSULIN PUMP, CPAP, ICD, AED, SALINE PUMP, ETC.) *<br>* OTHER MOBILE APP.S (E.G. APPLE HEALTH, MY FITNESS, ETC.)<br>* OTHER CONNECTED CONSUMER DEVICES (E.G. PERSONAL FITNESS DEVICES, SMART WATHCES, AMAZON ALEXA, GOOGLE HOME, SMART TV, HOME ENT. SYSTEM, CAR, ETC.) |
| CLOUD | (NONE DIRECTLY) | CLOUD |

FIG. 1A

| COMPONENT | SAMPLE USER(S) | COMPONENT EXAMPLES |
|---|---|---|
| EXTERNAL COMPONENT(S) OR SERVICE(S) | * MANUF. REP.S* | * GPS / LOC'N SERVICES<br>* CERTIFICATE AUTHORITY<br>* EMR SERVICES |
| CUSTOMER / CLINIC WEB COMPONENT(S) | * PHYSICIAN / HEALTH CARE PROVIDERS<br>* MANUF. REP.S* | * WCD CARE STATION<br>* NETWORK COMMUNICATION SYSTEM (E.G. LIFENET®, CARELINK®) |
| DEV. MANUF. WEB COMPONENT(S) | * PHYSICIAN / HEALTH CARE PROVIDERS<br>* MANUF. REP.S* | * WCD SYSTEM ADMIN STATION |
| PATIENT WEB COMPONENT(S) | * PATIENT<br>* CARE GIVERS<br>* PHYSICIAN / HEALTH CARE PROVIDERS<br>* MANUF. REP.S* | * PERSONALIZED PORTION OF WEBSITE<br>* OTHER COMPONENT WEBSITES (E.G. FITBIT ONLINE) |

FIG. 1B

SAMPLE COMPONENTS OF WEARABLE CARDIOVERTER DEFIBRILLATOR (WCD) SYSTEM

SAMPLE COMPONENTS OF EXTERNAL DEFIBRILLATOR

*SAMPLE LOCAL COMMUNICATION LINKS*

FIG. 11 *METHODS*

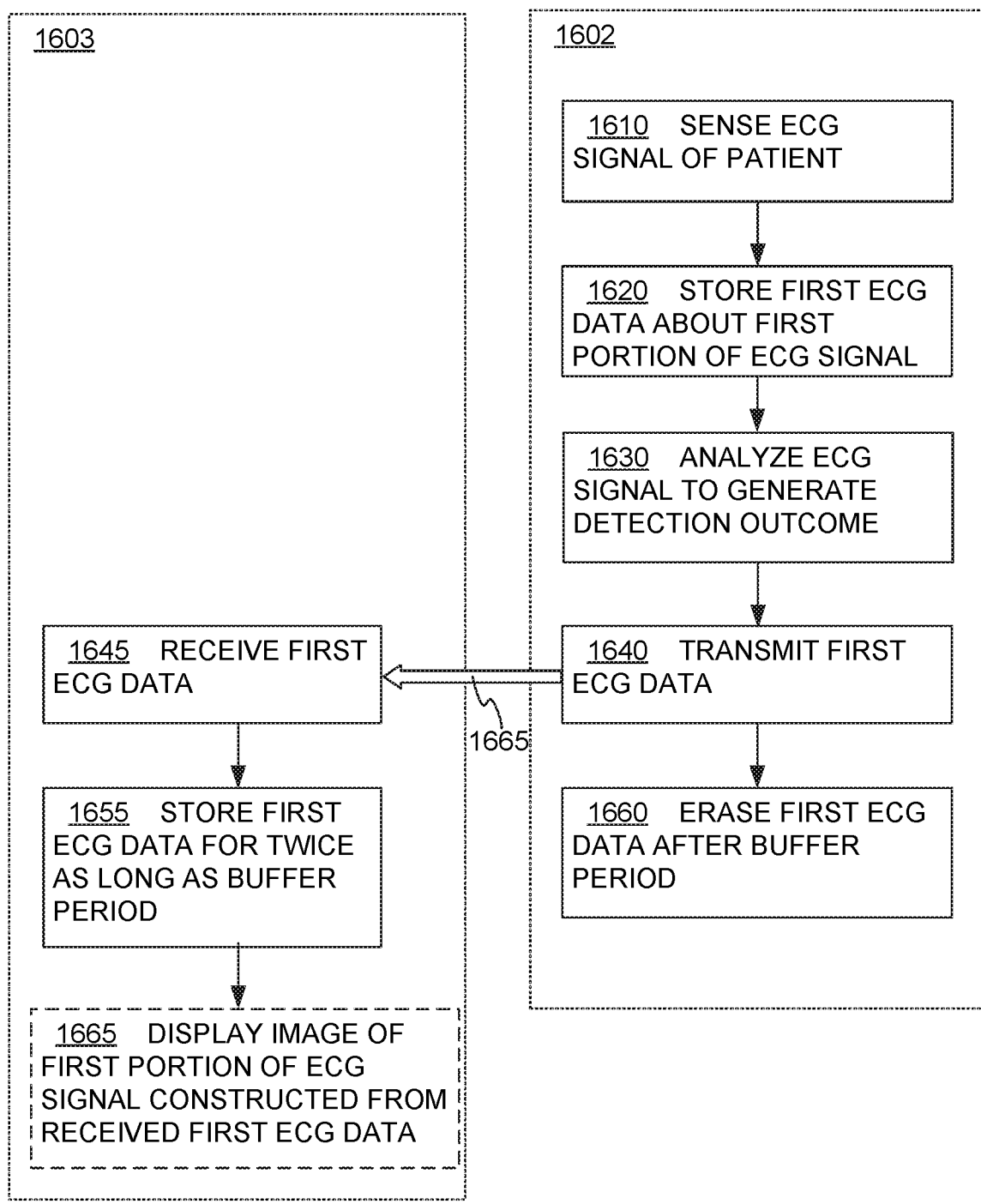
FIG. 16    METHODS

SAMPLE PROGRAMMING SCREEN

FIG. 21 *METHODS*

WEARABLE CARDIOVERTER DEFIBRILLATION (WCD) SYSTEM WITH PROXIMATE PROGRAMMING DEVICE WHICH STORES ECG DATA THAT THE WCD SYSTEM NORMALLY DISCARDS

CROSS-REFERENCE(S) TO RELATED APPLICATION(S)

This application is a continuation of U.S. patent application Ser. No. 16/010,254, filed Jun. 15, 2018, which claims priority from U.S. Provisional Patent Application Ser. No. 62/538,131, filed on Jul. 28, 2017, the entire disclosures of which are hereby incorporated by reference herein for all purposes.

BRIEF SUMMARY

The present description gives instances of wearable medical systems, programming devices for them, storage media that may store programs, and methods, the use of which may help overcome problems and limitations of the prior art.

In embodiments, a wearable medical system (WMS) for an ambulatory patient, which can be a wearable cardioverter defibrillator (WCD) system, senses the patient's ECG signal, and analyzes it to generate a detection outcome. The WMS may further have an ambulatory memory and an ambulatory user interface. A programming device, such as a PC, a tablet, etc., may include a programming user interface with a programming screen, and establish a communication link with the WMS. The communication link can be short range in view of programming the WMS during an in-person session with the patient.

In some of these embodiments the ambulatory user interface outputs a human-visible indication, and the programming screen reproduces the human-visible indication in real time. An advantage can be that the person programming the WMS need not strain to also look at the ambulatory user interface to determine whether or not the human-visible indication is output, at the time that they are looking at the programming device. Another advantage can be that the patient will recognize they are better protected, have their confidence in the WMS increased, and therefore better comply with wearing the WMS as required.

In some of these embodiments the WMS routinely discards ECG data after storing it for only a buffer period. That is because the WMS keeps only certain types of data to conserve space. The programming device, however, may store all the ECG data and for a longer time. An advantage can be that all ECG data can be analyzed, even if the WMS has not kept it.

In some of these embodiments the WMS can store a first parameter value as a rhythm analysis parameter. A processor uses the stored first parameter value to analyze the ECG signal so as to generate a detection outcome that has a first detection value, which is transmitted to, and displayed by the programming device. Then a programming input that is entered in the programming device can be transmitted back to the WMS and cause a second parameter value to be stored as the rhythm analysis parameter, in lieu of the first parameter value. Then the analysis of the ECG signal can generate a detection outcome that has a second detection value different from the first detection value. When that is transmitted to, and displayed by the programming device, the person operating it may make a better choice as to what parameter value to program the WMS with.

These and other features and advantages of the claimed invention will become more readily apparent in view of the embodiments described and illustrated in this specification, namely in this written specification and the associated drawings.

BRIEF DESCRIPTION OF THE DRAWINGS

FIGS. 1A & 1B show a table of a summary of possible components, sample users, and component examples of wearable medical devices according to embodiments.

FIG. 16 is a diagram for illustrating additional methods according to embodiments.

DETAILED DESCRIPTION

Figure 2A:
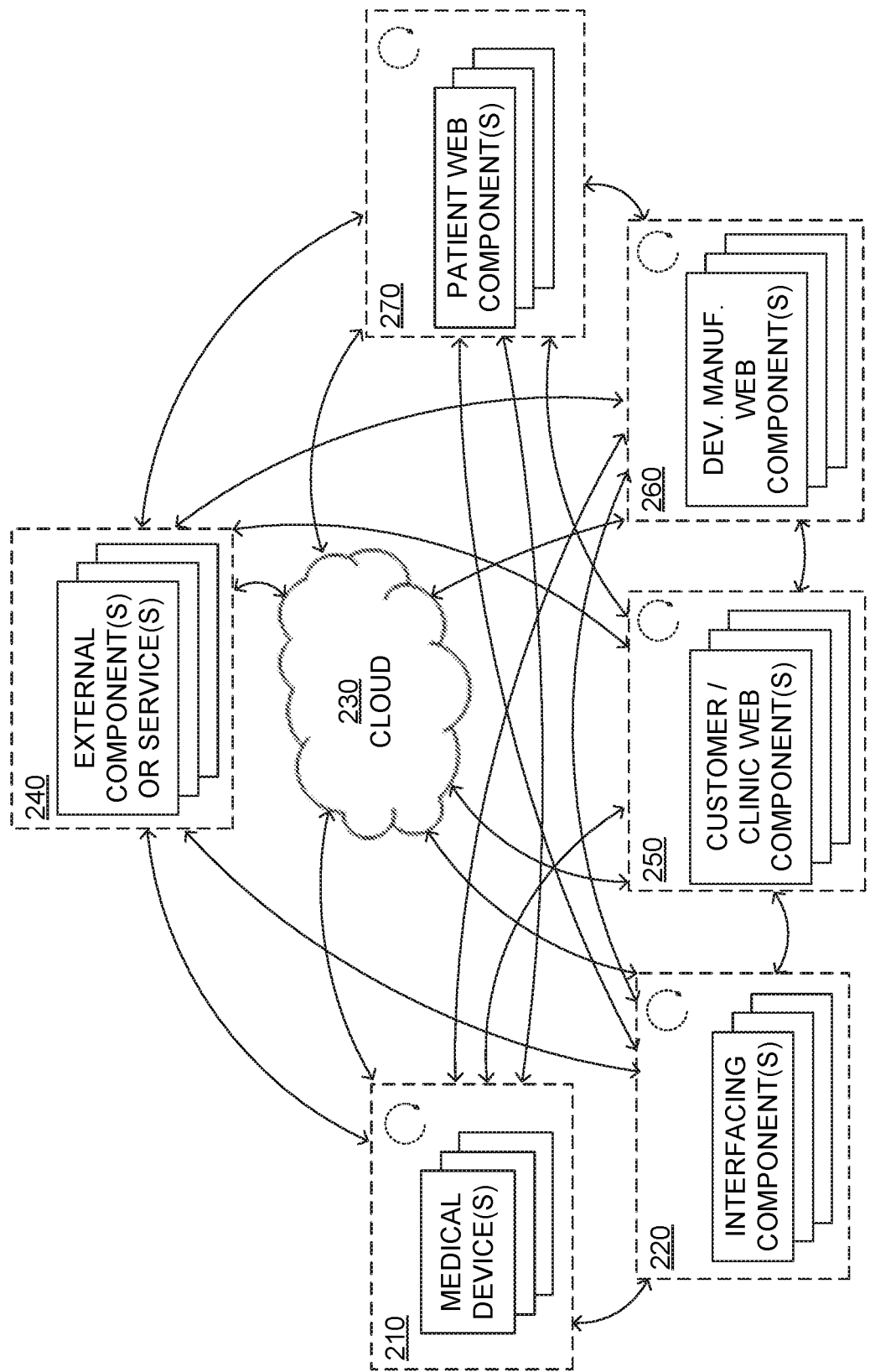
FIGS. 2A-2E show possible connection schemes among the components of FIGS. 1A & 1B according to embodiments.

As has been mentioned, the present description is about wearable medical devices, systems, storage media that may store programs, and methods, and also for programming devices, storage media and methods for programming the medical devices, systems, etc. Embodiments are now described in more detail.

Wearable medical devices can be configured to be worn by ambulatory patients. By being worn, a medical device is more ready to diagnose the patient. In some embodiments, the worn device are is actually part of a wearable medical system.

In some embodiments, a wearable medical system (WMS) is a Wearable Cardioverter Defibrillator (WCD) system. Early versions of such systems were called wearable cardiac defibrillator systems. When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some people have an increased risk of SCA. People at a higher risk include patients who have had a heart attack, or a prior SCA episode. A frequent recommendation is for these people to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart. After being identified as having an increased risk of an SCA, and before receiving an ICD, these people are sometimes given a Wearable Cardioverter Defibrillator system. (Early versions of such systems were called wearable cardiac defibrillator systems.) A WCD system typically includes a harness, vest, or other garment that the patient is to wear. Like other wearable medical systems, a WCD system according to embodiments includes a harness, vest, or other garment that the patient is to wear. The WCD system further includes electronic components, such as a defibrillator and electrodes, coupled to the harness, vest, or other garment. When the patient wears the WCD system, the external electrodes may then make good electrical contact with the patient's skin, and therefore can help sense the patient's ECG. If a shockable heart arrhythmia is detected, then the defibrillator delivers the appropriate electric shock through the patient's body, and thus through the heart.

In embodiments, a wearable medical system (WMS) has local and remote components that support acquisition, transmission, storage, augmentation, aggregation, and/or presentation of data throughout system components.

Components:

FIGS. 1A and 1B show a table of a summary of possible components, sample users, and component examples of wearable medical devices according to embodiments. Where FIGS. 1A and 1B show an asterisk (*), it means that employees, contractors, or other entities could be conducting work on behalf of a manufacturer. In addition, other components may facilitate the communication between each of the primary components listed in FIGS. 1A and 1B. For example, a desktop PC may be used to facilitate the connection between the Assure Tablet and the Certificate Authority. These components include:

A) Medical Device(s)—The cornerstone component of the medical device system that generates physiologic patient-associated data and device data for transmission throughout the medical device system. This component is typically a local component.

B) Interfacing Component(s)—The component that communicates between the cornerstone medical device and other components in the medical device system. Note that this component can itself be a medical device and is typically a local component.

C) Cloud—The remote component representing the storage and access of data via the internet.

D) Web Component(s), such as
  i) Customer/Clinic Web Component(s)—A local or remote web component used primarily by non-manufacturer affiliated personnel that manage the care of the patient using one or more of the medical device components in the medical device system.
  ii) Device Manufacturer Web Component(s)—A local or remote web component used primarily by manufacturer affiliated personnel that manage any of the components of the medical device system.
  Iii) Patient Web Component(s)—A local or remote web component used primarily by the patient that is using one or more of the medical device components in the medical device system.

E) External Component(s) or Service(s)—Remote component(s) or service(s) that contribute to the medical device system in some capacity.

Interconnections:

The components of FIGS. 1A & 1B can be interconnected in a number of ways, in other words, by establishing different sets of communication pathways among them. Such communication pathways can be achieved in part or in total by a number of ways, including the following, alone or in combination: Wi-Fi, cellular, Bluetooth (Classic, Low Energy), Near-Field Communication, Hardwired Connection (like USB), etc. Some such ways are now described:

Referring to FIG. 2A, a connection scheme is shown where every one of: medical devices 210, interfacing components 220, external components or services 240, customer/clinic web component(s) 250, Device Manufacturer Web Component(s) 260 and Patient Web Component(s) 270 is connected to the other, and all are connected to cloud 230.

Figure 2B:
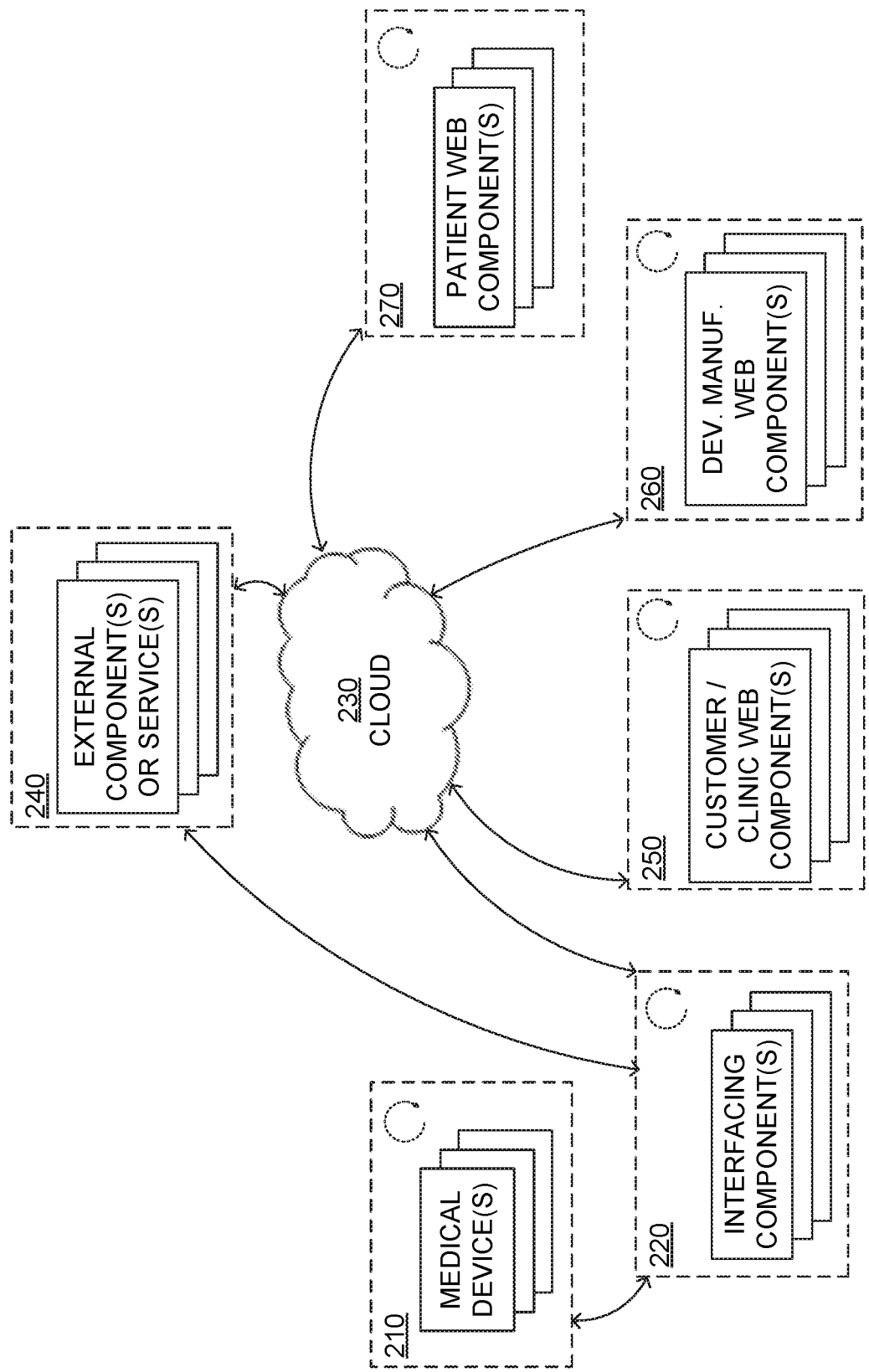

Referring to FIG. 2B, another connection scheme is shown among the components of FIG. 2A. This connection scheme, however, is simpler.

Figure 2C:
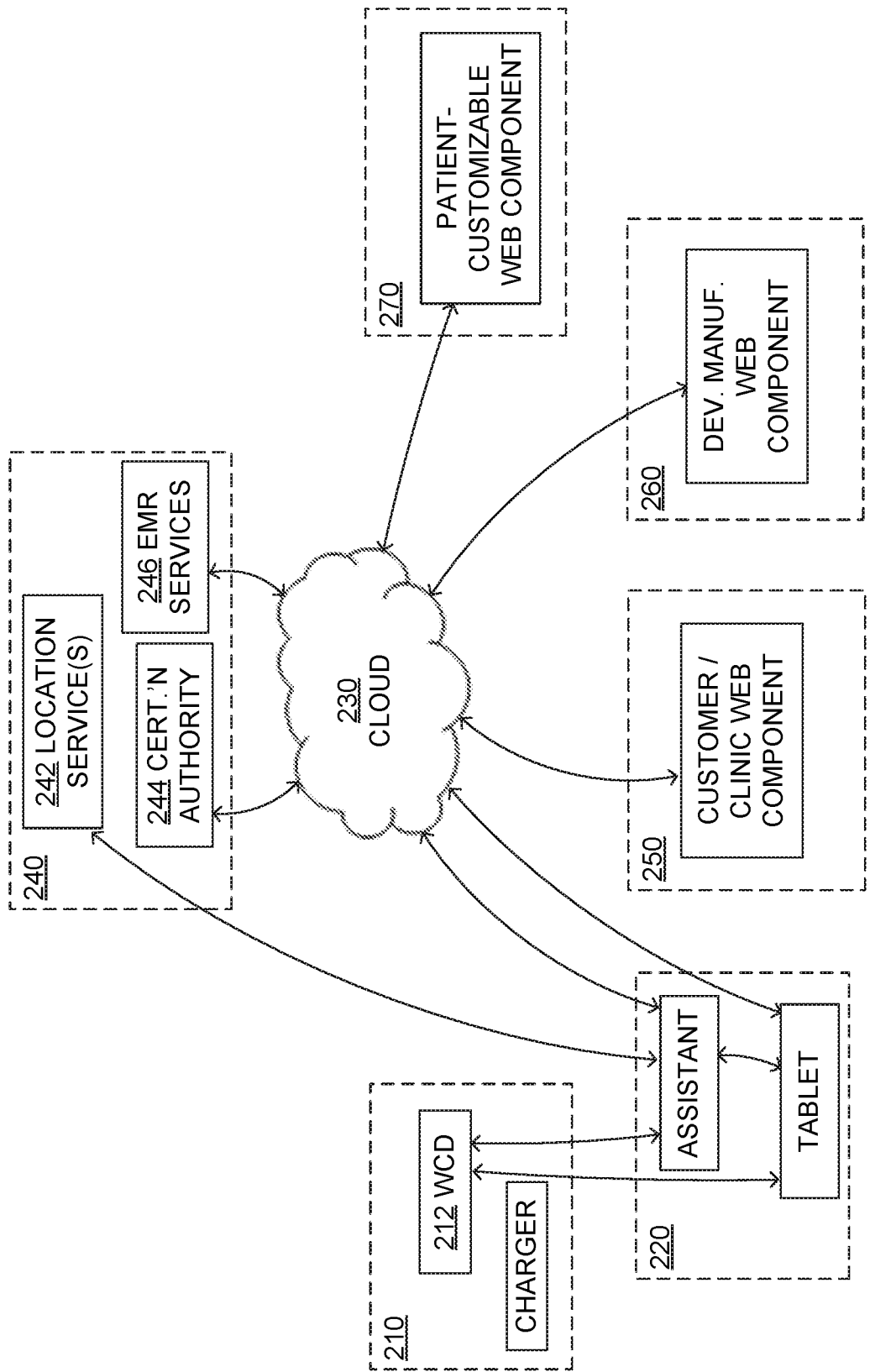

Referring to FIG. 2C, one more connection scheme is shown. Medical devices 210 include a WCD 212, and possibly also a charger. In addition to what was described above, interfacing components 220 may include an assistant that is an electronic device, and/or a tablet that can be custom, or generic running a custom application ("app"). External components or services 240 may include one or more of location services 242, certification authority 244, EMR services 246, etc.

Figure 2D:
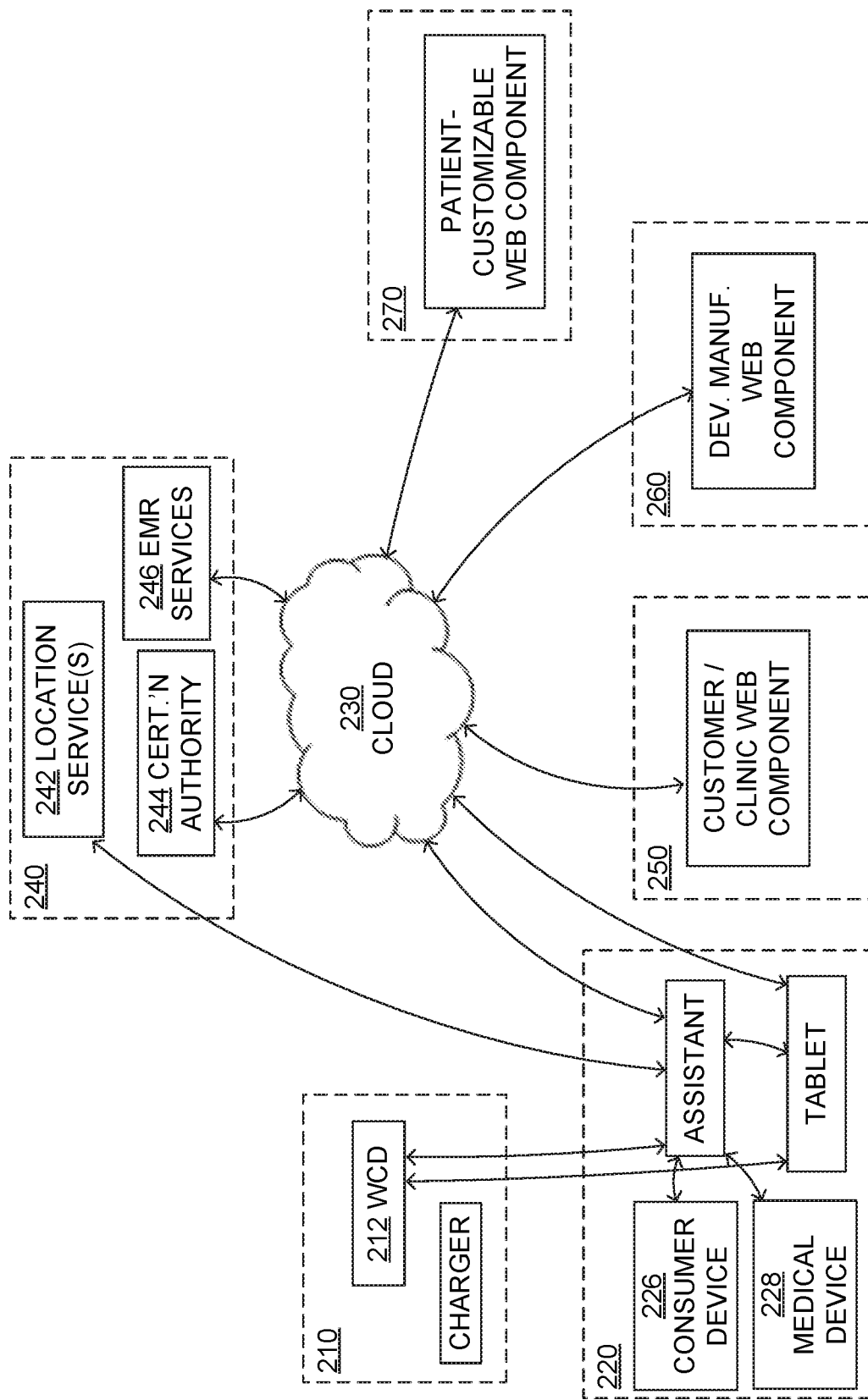

Referring to FIG. 2D, an additional connection scheme is shown. Further to what was described above, this scheme incorporates additional interfacing components 220, such as a consumer device 226 and/or a medical device 228. These may contribute additional communication pathways of WCD 212 to cloud 230.

Figure 2E:
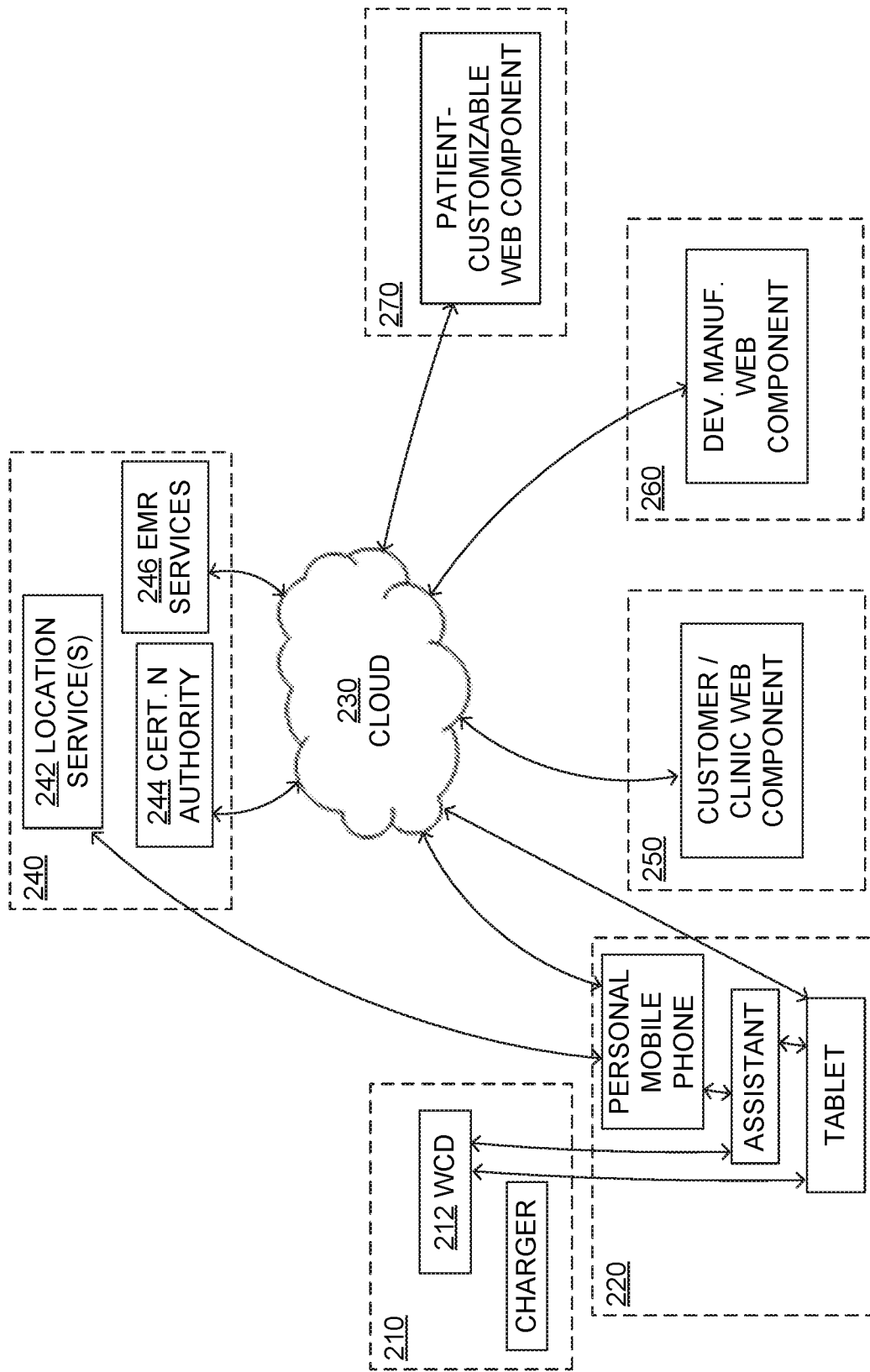

Referring to FIG. 2E, one more connection scheme is shown. In this example, the only connection of WCD 212 with cloud 230 is via a personal mobile phone. This implementation can also be applied to the tablet.

Triggering Communication:

Communication may be triggered in a number of ways along these pathways. For example, upon manual request via an interfacing component, upon remote request through a web component, upon automatic interfacing component request of the Medical Device component. For instance, an assistant device or tablet may request data from the WCD for purposes of transmitting to a server without user intervention. Such an automatic request can be driven by any one or combination of the following methods: detection of a specific event, like shock delivery, a time schedule, e.g. every 2 hours, reaching a geographic location, e.g. returning home, according to a priority scheme, like waiting to transmit all data until a certain higher priority event occurs.

The above-described communication pathways can be used for the acquisition, transmission, storage, augmentation, aggregation, and/or presentation of data associated with a medical device and/or any of the interfacing components and web interfaces. This data can be generally broken down into several categories:

A) Physiologic data acquired by any component.

B) Event, device operational, environmental, or other non-physiologic data acquired by any component.

C) Manual input of data into a component.

For purposes of acquisition of data, a component in a medical device system made according to embodiments can acquire data about itself, physiologic data about the patient. In another example, an assistant device may acquire event data about its own operation. Plus, component(s) in the medical device system may acquire data about other components in the system. For example, a WCD may acquire event log data regarding connectivity status with an assistant device, a tablet, etc.

For purposes of transmission of data, component(s) in a medical device system made according to embodiments can transmit data from itself to another component. For example, a WCD can transmit data to an assistant device, a tablet, etc.

For purposes of storage of data, component(s) in a medical device system made according to embodiments can store acquired data on itself. For example, an assistant device, a tablet, etc. may store event data about its own operation on itself. They may also extract data intended for transmission to another component for storage. For example, an assistant device or a tablet may transmit data from a WCD to a server. In the process, the an assistant device or a tablet may extract specific data for storage on itself. They may also manage their own storage based on storage of data on other components. For example, an assistant device or a tablet may report data until the report is transmitted to a server. Upon successful transmission, the an assistant device or a tablet may delete some of the report data stored on itself.

For purposes of augmentation of data a component in a medical device system made according to embodiments may augment data that was acquired on another component. For example, an assistant device or a tablet may augment an emergency event marker with location data acquired by it. This full set of data may then be transmitted to a server. Other examples of the use of an interfacing component to add patient-provided or interfacing-component provided information/data to a patient record include: adding select symptoms from a list or free type symptoms; add video/voice recording/pictures; add location (GPS, altitude, address, distance from home, etc.); add weather information (temp, pressure, humidity, etc.), etc.

For purposes of aggregation of data, component(s) in a medical device system made according to embodiments can aggregate data that acquired on itself or another component. For example, a server may aggregate all data acquired by a specific WCD for presentation with a single patient record.

For purposes of presentation of data, component(s) in a medical device system made according to embodiments may present data acquired on itself or another component. For example, a server or a table may present: log data acquired on themselves, acquired WCD data, acquired data from an assistant device or a tablet, etc.

Embodiments enable a number of features:

First, automatic notifications of specific events. These may happen via any one of: push/pop-up on interfacing component or medical device, web notification, email notification, text notification, cellular phone calls, etc.

Second, patient can be set up in a remote monitoring system at any time (before or after providing the patient with the device).

Third, automatic generation of a patient record in the Cloud or Customer/Clinic web component.

Fourth, automatic emergency response from the Medical Device→Interfacing Component→Cloud→Device Manufacturer Web Component→Operator→EMS.

Fifth, automatic generation of equipment status notifications to the Device Manufacturer Web Component; these equipment status notifications could include notifications for battery capacity, amount of leads-off alerts, defibrillator pad contact/status alerts, service needed, service required, shocks delivered.

Sixth, automatic generation and transmission of medical device equipment status (data) via Medical Device→Interfacing Component→Cloud→Device Manufacturer Web Component.

Seventh, ability to remotely managing patient access to data on a patient-by-patient basis by using the web components to manage the interfacing components or medical devices. For example, a server may provides an ability for the physician to use of preferences to control what a specific patient can see on their assistant device or tablet.

Eighth, ability to facilitate data, communication, or notifications from any component to any component. For example, data, communication, or notifications can be transmitted: a) from the Patient to the Clinic and/or the Manufacturer; b) from the Clinic to the Patient and/or the Manufacturer; c) from the Manufacturer to the Patient and/or the Clinic; d) From a Clinic Web Component to another Clinic Web Component; like data from one hospital to another; e) from an Interfacing Component to another Interfacing Component; like data from a consumer medical device to the assistant device or tablet, etc.

Embodiments present advantages over prior art, for example:

Cohesive system architecture in which data acquired by a medical device and any number of compatible interfacing components is stored in a central location and accessed on-demand via multiple web interfaces.

Ability for interfacing components and web interfaces to manage the acquisition of data from a medical device.

Ability for interfacing components and web interfaces to acquire, transmit, store, augment, aggregate, and/or present data associated with a medical device and/or any of the interfacing components and web interfaces.

Ability to add of any number of interfacing components and medical devices in the same medical device system— data acquired by and about all devices in the medical device system can be accessed from a central location.

While the availability of cloud 230 creates great flexibility, when it comes to programming a wearable medical device (WMS) so as to customize it to an individual patient, there are advantages to programming the WMS in an in-person session with the patient. These advantages include the confidence that the right WMS is being programmed, and for the right patient. These advantages further include the confidence that the patient may develop from the in-person session about wearing the WMS as required. These advantages further include the security that arises from perhaps possible outside malfeasance.

In embodiments, therefore, a wearable medical device (WMS) is programmed by a programming device over a local communication link. Examples are now described.

Figure 3:
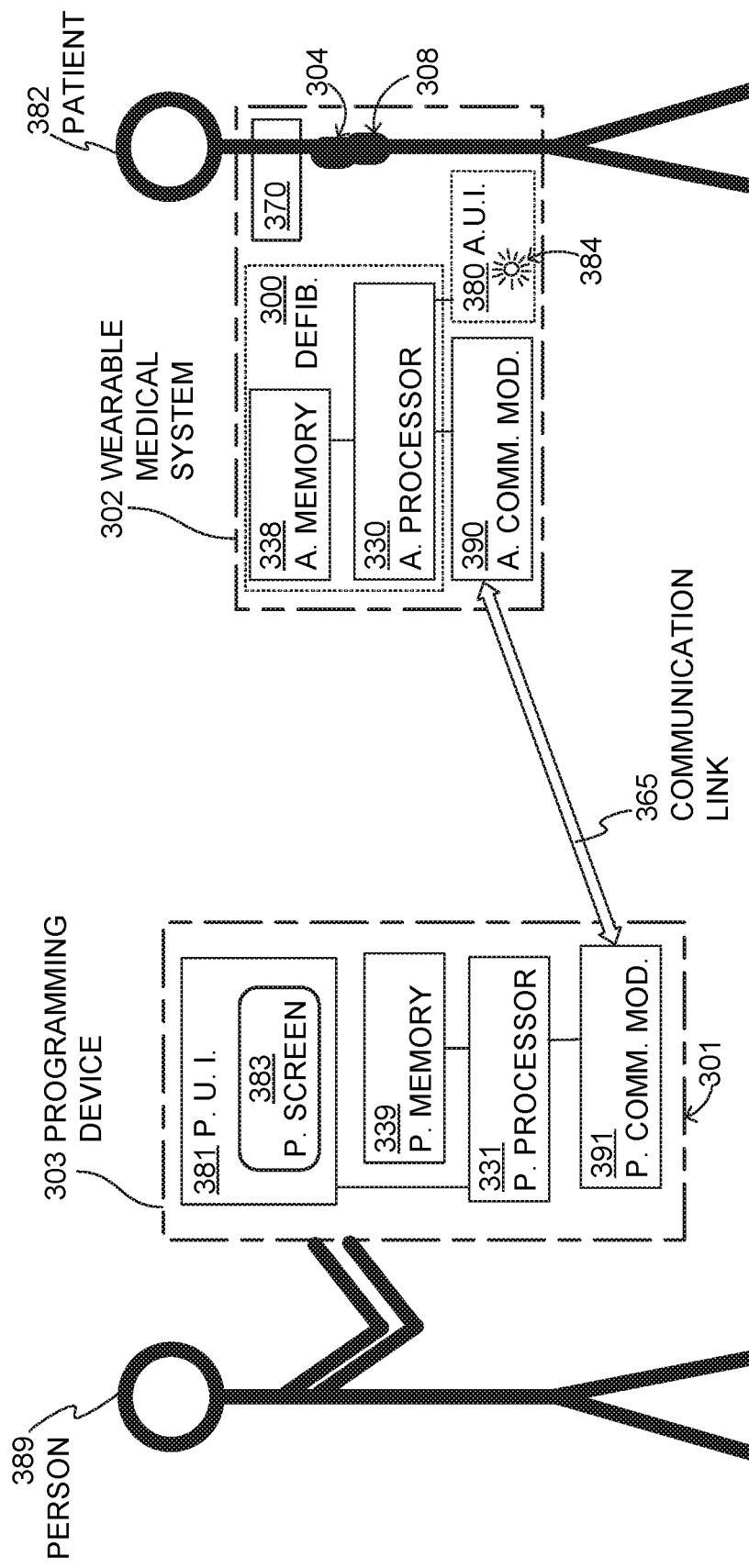
FIG. 3 is a diagram of a sample wearable medical system (WMS) in combination with a proximate programming device that may be used to program the wearable medical system by communicating with it, according to embodiments.

FIG. 3 depicts a patient 382 wearing a sample wearable medical system (WMS) 302. Patient 382 is ambulatory, which means patient 382 can walk around, and is not necessarily bed-ridden. In addition, a person 389 operates a programming device 303 to program WMS 302. Person 389 can be a trained clinician, etc.

WMS 302 has a number of components. These components can be provided together, all or in groups, separately as modules that can be interconnected, etc.

One such component of WMS 302 is a support structure 370 that is wearable by patient 382. It will be understood that support structure 370 is shown only generically in FIG. 3, and in fact partly conceptually. FIG. 3 is provided merely to illustrate concepts about support structure 370, and is not to be construed as limiting how support structure 370 is implemented, or how it is worn. Support structure 370 can be implemented in many different ways. For example, it can be implemented in a single component or a combination of multiple components. In embodiments, support structure 370 could include a vest, a half-vest, a garment, etc. In such embodiments such items can be worn similarly to parallel articles of clothing. In embodiments, support structure 370 could include a harness, one or more belts or straps, etc. In such embodiments, such items can be worn by the patient around the torso, hips, over the shoulder, etc. In embodiments, support structure 370 can include a container or housing, which can even be waterproof. In such embodiments, the support structure can be worn by being attached to the patient by adhesive material, for example as shown in U.S. Pat. No. 8,024,037. Support structure 370 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/ 0056682 document. There can be other examples. In embodiments, support structure 370 can be fitted to the body of patient 382.

Another such component of WMS 302 is electrodes 304, 308, which can be coupled to support structure 370. Some of these electrodes 304, 308 can be configured to sense an electrocardiogram (ECG) signal of patient 382.

One more component of WMS 302 can be an ambulatory processor 330. Ambulatory processor 330 can be configured to analyze the sensed ECG signal, so as to generate a detection outcome from the sensed ECG signal, as described in more detail later in this document. Processor 330 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

An additional component of WMS 302 can be an ambulatory memory 338. Memory 338 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 338 is thus a non-transitory storage medium. Memory 338, if provided, can store instructions for processor 330, which processor 330 may be able to read and execute. The instructions, which may also referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. A set of such instructions can also be called a program. More particularly, the programs can include sets of instructions in the form of code, which processor 530 may be able to execute upon reading. Processor 330 may store programs that can be operational for the inherent needs of processor 330. Executing is performed by physical manipulations of physical quantities, and may result in functions, operations, processes, actions and/or methods to be performed, and/or the processor to cause other devices or components or blocks to perform such functions, operations, processes, actions and/ or methods. Processor 330 may include, or have access to, a non-transitory storage medium, such as memory 338. Such a memory can have a non-volatile component for storage of machine-readable and machine-executable instructions.

In embodiments where WMS 302 is a wearable cardioverter defibrillator (WCD) system, then WMS 302 further includes a defibrillator 300. In such embodiments, ambulatory processor 330 and ambulatory memory 338 can be components of defibrillator 300. One or more of electrodes 304, 308 can be configured for conducting an electrical charge. As such, defibrillator 300 can configured to discharge, through patient 382 via at least some of electrodes 304 308, an electrical charge while support structure 370 is worn by patient 382 so as to deliver a shock to patient 382. Of course, such a discharge would happen responsive to a detection outcome by processor 330.

In embodiments, operational parameters of a WMS can be customized for patient 382. For example, baseline physiological parameters of patient 382 can be measured, such as the heart rate of patient 382 while resting, while walking, motion detector outputs while walking, etc. Such baseline physiological parameters can be used to customize the WCD system, in order to make its diagnoses more accurate, since the patients' bodies differ from one another. Of course, such parameters can be stored in ambulatory memory 338, and so on.

In embodiments where WMS 302, one more component of WMS 302 is an ambulatory user interface 380. Ambulatory user interface 380 can be coupled to the support structure 370, to defibrillator 300, to both, etc. Ambulatory user interface 380 may be adjusted for use by a user such as patient 382, person 389, a bystander if patient 382 is unexpectedly unconscious in a public place, and so on.

User interface 380 can be made in a number of ways. User interface 380 may include output devices, which can be visual, audible or tactile, for communicating to a user by outputting images, sounds or vibrations. Images, sounds, vibrations, and anything that can be perceived by the user can also be called human-perceptible indications. There are many examples of output devices. For example, an output device can be a light, or a screen to display what is sensed, detected and/or measured, and provide visual feedback to a rescuer for their resuscitation attempts, and so on. As such, ambulatory user interface 380 can be configured to output a human-visible indication 384. Another output device can be a speaker, which can be configured to issue voice prompts, beeps, loud alarm sounds and/or words to warn bystanders, etc.

User interface 380 may further include input devices for receiving inputs from its users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

It will be appreciated that aspects of user interface 380 that are designed for easy viewing by patient 382 are not always necessarily the easiest viewable by person 389.

A further component of WMS 302 can be an ambulatory communication module 390. Ambulatory communication module 390 can be coupled to support structure 370, to defibrillator 300 if provided, to both, etc. Ambulatory communication module 390 may be configured to establish one or more wired or wireless communication links with other devices of other entities, such as a remote assistance center, Emergency Medical Services (EMS), and so on. The data can include patient data, event information, therapy attempted, Cardiopulmonary resuscitation (CPR) performance, system data, environmental data, and so on. For example, communication module 390 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 390 may also include such interconnected sub-components as may be deemed necessary by a person skilled in the art, for example an antenna, portions of a processor, supporting electronics, outlet for a telephone or a network cable, etc. This way, data, commands, etc. can be communicated to other entities.

Programming device 303 may be have a housing 301, and be implemented in a number of ways. It may be provided together with the components of WMS 302, as a custom device—for instance it may look like a tablet. Or, it may be a generic computer that is running custom applications. As a generic computer, it may be a PC, a desktop, a laptop, a tablet, a smartphone, and so on. Even if provided together with the components of WMS 302, in some embodiments programming device 303 is operable while it is not coupled to support structure 370, in other words programming device 303 is typically not carried or worn by patient 382.

As such, in some embodiments programming device 303 may include a programming processor 331 and a programming memory 339, which can be made at least as is known for commercially available computers.

In addition, programming device 303 may include a programming communication module 391. Again, programming communication module 391 can be made as is known for commercially available computers. In embodiments, programming communication module 391 may be able to establish a local communication link 365 with ambulatory communication module 390. After that, data and commands may be exchanged over local communication link 365. For example, baseline physiological parameters measured by WMS 302 may be received over local communication link 365, and stored in programming memory 339.

Moreover, programming device 303 may include a programming user interface 381. Again, programming user interface 381 can be made as is known for commercially available computers, with output devices such as screens, speakers and vibration detectors, and input devices such as buttons, a keyboard, a keypad, a mouse and the like. A touchscreen is an example of both an input device and an output device. Programming user interface 381 can be configured to receive inputs entered by person 389, such as programming inputs ("Enter" key), activation inputs (e.g. mouse clicks), other types of inputs described herein, etc. In particular, programming user interface 381 may include a programming screen 383 that is arranged for viewing by person 389.

As mentioned above, an example of a wearable medical system according to embodiments is a wearable cardioverter defibrillator (WCD) system. A wearable cardioverter defibrillator (WCD) system made according to embodiments has a number of components. These components can be provided separately as modules that can be interconnected, or can be combined with other components, etc. Examples are now described.

Figure 4:
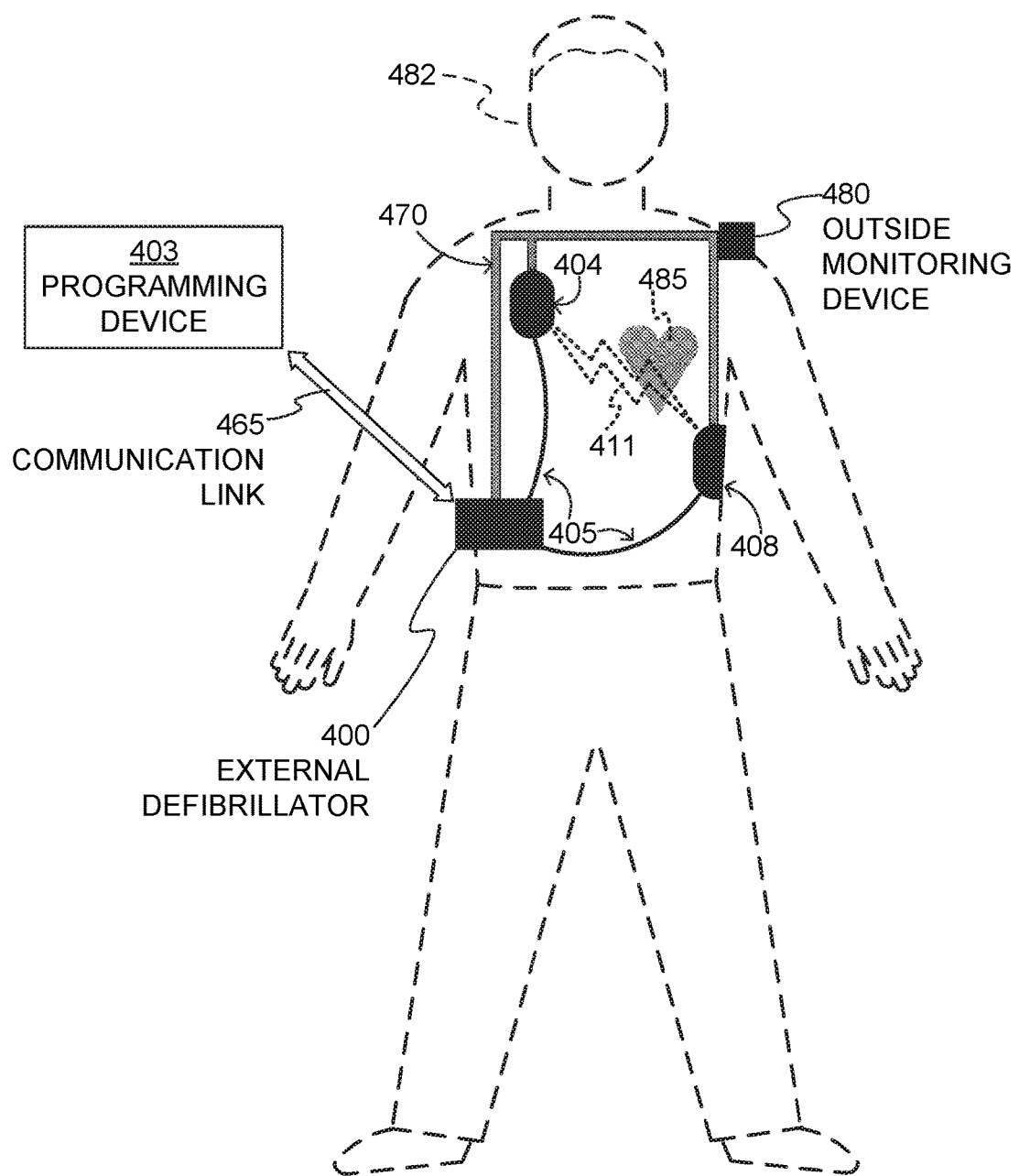
FIG. 4 is a diagram of components of a sample wearable cardioverter defibrillator (WCD) system that could be the WMS of FIG. 3, made according to embodiments.

FIG. 4 depicts an ambulatory patient 482. Patient 482 may also be referred to as a person and/or wearer, since the patient is wearing components of the WCD system. FIG. 4 also depicts components of a WCD system made according to embodiments. One such component is a support structure 470 that is wearable by patient 482, and can be as described above for support structure 370.

A WCD system according to embodiments is configured to defibrillate patient 482 who is wearing it, by delivering an electrical charge to the patient's body in the form of an electric shock delivered in one or more pulses. FIG. 4 shows a sample external defibrillator 400, and sample defibrillation electrodes 404, 408, which are coupled to external defibrillator 400 via electrode leads 405. Defibrillator 400 and defibrillation electrodes 404, 408 can be coupled to support structure 470. As such, many of the components of defibrillator 400 could be therefore coupled to support structure 470. When defibrillation electrodes 404, 408 make good electrical contact with the body of patient 482, defibrillator 400 can administer, via electrodes 404, 408, a brief, strong electric pulse 411 through the body. Pulse 411 is also known as shock, defibrillation shock, therapy and therapy shock. Pulse 411 is intended to go through and restart heart 485, in an effort to save the life of patient 482. Pulse 411 can further include one or more pacing pulses, and so on.

In the example of FIG. 4, a programming device 403 is also shown. Programming device 403 can be as the previously described programming device 303. Programming device 403 can be able to establish a local communication link 465, similar to local communication link 365, with at least one of the worn components of the WCD system. In the example of FIG. 4, such a worn component is external defibrillator 400.

A prior art defibrillator typically decides whether to defibrillate or not based on an ECG signal of the patient. However, wearable external defibrillator 400 may initiate defibrillation (or hold-off defibrillation) based on a variety of inputs, with ECG merely being one of them. Accordingly, it will be appreciated that signals such as physiological signals containing physiological data can be obtained from patient 482. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 480. Device 480 is called an "outside" device because it could be provided as a standalone device, for example not within the housing of defibrillator 400. Device 480 can be configured to sense or monitor at least one local parameter. A local parameter can be a parameter of patient 482, or a parameter of the WCD system, or a parameter of the environment, as will be described later in this document. Device 480 may include one or more transducers or sensors that are configured to render one or more physiological inputs or signals from one or more patient parameters that they sense.

Optionally, device 480 is physically coupled to support structure 470. In addition, device 480 can be communicatively coupled with other components, which are coupled to support structure 470. Such communication can be implemented by a communication module, as will be deemed applicable by a person skilled in the art in view of this description.

Figure 5:
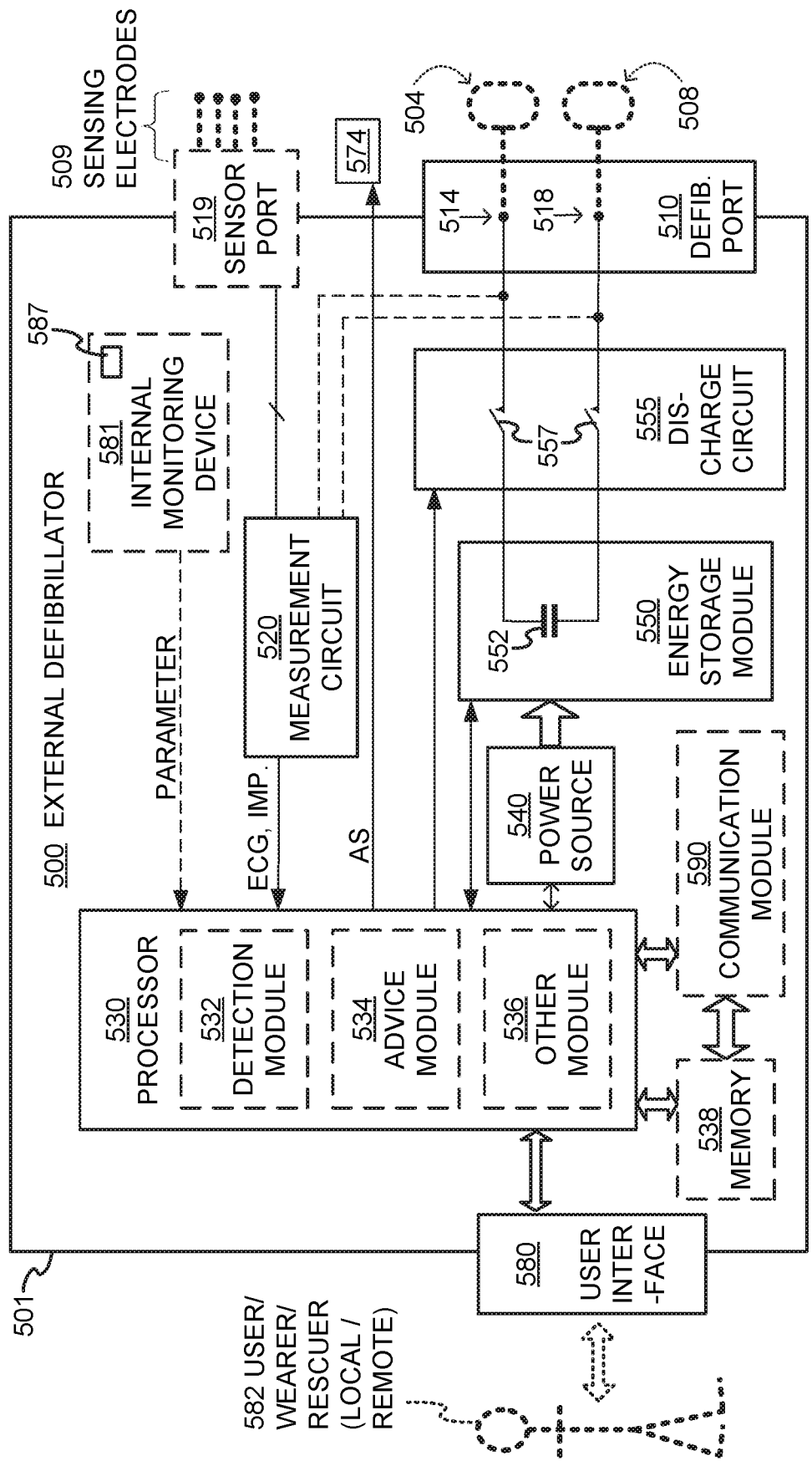
FIG. 5 is a diagram showing sample components of an external defibrillator, such as the one belonging in the system of FIG. 4, and which is made according to embodiments.

FIG. 5 is a diagram showing components of an external defibrillator 500, made according to embodiments. These components can be, for example, included in external defibrillator 400 of FIG. 4. The components shown in FIG. 5 can be provided in a housing 501, which may also be referred to as casing 501.

External defibrillator 500 is intended for a patient who would be wearing it, such as patient 482 of FIG. 4. Defibrillator 500 may further include a user interface 580 for a user 582. User 582 can be patient 482, also known as wearer 482. Or, user 582 can be a local rescuer at the scene, such as a bystander who might offer assistance, or a trained person. Or, user 582 might be a remotely located trained caregiver in communication with the WCD system. User interface 580 can be made as described above for ambulatory user interface 380.

Defibrillator 500 may include an internal monitoring device 581. Device 581 is called an "internal" device because it is incorporated within housing 501. Monitoring device 581 can sense or monitor patient parameters such as patient physiological parameters, system parameters and/or environmental parameters, all of which can be called patient data. In other words, internal monitoring device 581 can be complementary or an alternative to outside monitoring device 480 of FIG. 4. Allocating which of the parameters are to be monitored by which of monitoring devices 480, 581 can be done according to design considerations. Device 581 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 480, 581 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 582. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 582 will know about a condition that is either not improving or deteriorating.

Patient state parameters include recorded aspects of patient 582, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 480 or monitoring device 581. Such a motion detector can be made in many ways as is known in the art, for example by using an accelerometer. In this example, a motion detector 587 is implemented within monitoring device 581.

A motion detector of a WCD system according to embodiments can be configured to detect a motion event. In response, the motion detector may render or generate, from the detected motion event or motion, a motion detection input that can be received by a subsequent device or functionality. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed, if monitoring device 480 or 581 includes a GPS location sensor as per the above, and if it is presumed that the patient is wearing the WCD system.

Defibrillator 500 typically includes a defibrillation port 510, such as a socket in housing 501. Defibrillation port 510 includes electrical nodes 514, 518. Leads of defibrillation electrodes 504, 508, such as leads 405 of FIG. 4, can be plugged into defibrillation port 510, so as to make electrical contact with nodes 514, 518, respectively. It is also possible that defibrillation electrodes 504, 508 are connected continuously to defibrillation port 510, instead. Either way, defibrillation port 510 can be used for guiding, via electrodes, to the wearer the electrical charge that has been stored in an energy storage module 550 that is described more fully later in this document. The electric charge will be the shock for defibrillation, pacing, and so on.

Defibrillator 500 may optionally also have a sensor port 519 in housing 501, which is also sometimes known as an ECG port. Sensor port 519 can be adapted for plugging in sensing electrodes 509, which are also known as ECG electrodes and ECG leads. It is also possible that sensing electrodes 509 can be connected continuously to sensor port 519, instead. Sensing electrodes 509 are types of transducers that can help sense an ECG signal, e.g. a 12-lead signal, or a signal from a different number of leads, especially if they make good electrical contact with the body of the patient and in particular with the skin of the patient. Sensing electrodes 509 can be attached to the inside of support structure 470 for making good electrical contact with the patient, similarly with defibrillation electrodes 504, 508.

Optionally a WCD system according to embodiments also includes a fluid that it can deploy automatically between the electrodes and the patient's skin. The fluid can be conductive, such as by including an electrolyte, for establishing a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away from the electrode, after it has been deployed. The fluid can be used for both defibrillation electrodes 504, 508, and for sensing electrodes 509.

The fluid may be initially stored in a fluid reservoir, not shown in FIG. 5, which can be coupled to the support structure. In addition, a WCD system according to embodiments further includes a fluid deploying mechanism 574. Fluid deploying mechanism 574 can be configured to cause at least some of the fluid to be released from the reservoir, and be deployed near one or both of the patient locations, to which the electrodes are configured to be attached to the patient. In some embodiments, fluid deploying mechanism 574 is activated prior to the electrical discharge responsive to receiving activation signal AS from a processor 530, which is described more fully later in this document.

In some embodiments, defibrillator 500 also includes a measurement circuit 520, as one or more of its sensors or transducers. Measurement circuit 520 senses one or more electrical physiological signals of the patient from sensor port 519, if provided. Even if defibrillator 500 lacks sensor port 519, measurement circuit 520 may optionally obtain physiological signals through nodes 514, 518 instead, when defibrillation electrodes 504, 508 are attached to the patient. In these cases, the physiological input reflects an ECG measurement. The patient parameter can be an ECG, which can be sensed as a voltage difference between electrodes 504, 508. In addition the patient parameter can be an impedance, which can be sensed between electrodes 504, 508 and/or the connections of sensor port 519. Sensing the impedance can be useful for detecting, among other things, whether these electrodes 504, 508 and/or sensing electrodes 509 are not making good electrical contact with the patient's body. These patient physiological signals can be sensed, when available. Measurement circuit 520 can then render or generate information about them as physiological inputs, data, other signals, etc. More strictly speaking, the information rendered by measurement circuit 520 is output from it, but this information can be called an input because it is received by a subsequent device or functionality as an input.

Defibrillator 500 also includes a processor 530, which can be made as described above for ambulatory processor 330. Processor 530 can be considered to have a number of modules. One such module can be a detection module 532. Detection module 532 can include a Ventricular Fibrillation (VF) detector. The patient's sensed ECG from measurement circuit 520, which can be available as physiological inputs, data, or other signals, may be used by the VF detector to determine whether the patient is experiencing VF. Detecting VF is useful, because VF typically results in SCA. Detection module 532 can also include a Ventricular Tachycardia (VT) detector, and so on.

Another such module in processor 530 can be an advice module 534, which generates advice for what to do. The advice can be based on outputs of detection module 532. There can be many types of advice according to embodiments. In some embodiments, the advice is a shock/no shock determination that processor 530 can make, for example via advice module 534. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Processor 530 can include additional modules, such as other module 536, for other functions. In addition, if internal monitoring device 581 is indeed provided, it may be operated in part by processor 530, etc.

Defibrillator 500 optionally further includes a memory 538, which can work together with processor 530. Processor 530 may store programs that can be operational for the inherent needs of processor 530, and can also include protocols and ways that decisions can be made by advice module 534. In addition, memory 538 can store prompts for user 582, if this user is a local rescuer. Moreover, memory 538 can store data. This data can include patient data, system data and environmental data, for example as learned by internal monitoring device 581 and outside monitoring device 480. The data can be stored in memory 538 before it is transmitted out of defibrillator 500, or stored there after it is received by defibrillator 500.

Defibrillator 500 may also include a power source 540. To enable portability of defibrillator 500, power source 540 typically includes a battery. Such a battery is typically implemented as a battery pack, which can be rechargeable or not. Sometimes a combination is used of rechargeable and non-rechargeable battery packs. Other embodiments of power source 540 can include an AC power override, for where AC power will be available, an energy-storing capacitor, and so on. In some embodiments, power source 540 is controlled by processor 530. Appropriate components may be included to provide for charging or replacing power source 540.

Defibrillator 500 may additionally include an energy storage module 550. Energy storage module 550 can be coupled to the support structure of the WCD system, for example either directly or via the electrodes and their leads. Module 550 is where some electrical energy can be stored temporarily in the form of an electrical charge, when preparing it for discharge to administer a shock. In embodiments, module 550 can be charged from power source 540 to the desired amount of energy, as controlled by processor 530. In typical implementations, module 550 includes a capacitor 552, which can be a single capacitor or a system of capacitors, and so on. In some embodiments, energy storage module 550 includes a device that exhibits high power density, such as an ultracapacitor. As described above, capacitor 552 can store the energy in the form of an electrical charge, for delivering to the patient.

Defibrillator 500 moreover includes a discharge circuit 555. When the decision is to shock, processor 530 can be configured to control discharge circuit 555 to discharge through the patient the electrical charge stored in energy storage module 550. When so controlled, circuit 555 can permit the energy stored in module 550 to be discharged to nodes 514, 518, and from there also to defibrillation electrodes 504, 508, so as to cause a shock to be delivered to the patient. Circuit 555 can include one or more switches 557. Switches 557 can be made in a number of ways, such as by an H-bridge, and so on. Circuit 555 can also be controlled via user interface 580.

Defibrillator 500 can optionally include a communication module 590, which can be made as described above for ambulatory communication module 390. Communication module 590 may establish one or more wired or wireless communication links with other devices of other entities, such as a remote assistance center, Emergency Medical Services (EMS), and so on. Then it may transmit through these links data such as patient data, event information, therapy attempted, CPR performance, system data, environmental data, and so on. For example, communication module 590 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 590 may also include such interconnected subcomponents as may be deemed necessary by a person skilled in the art, for example an antenna, portions of a processor, supporting electronics, outlet for a telephone or a network cable, etc. This way, data, commands, etc. can be communicated.

Defibrillator 500 can optionally include other components.

Returning to FIG. 3, and as also mentioned above, there are advantages in making link 365 short, in connection with the programming being performed by person 389 in an in-person session with patient 382. As such, link 365 may be a few to several feet long, and in any event shorter than 99 feet in length. For purposes of this document, this means that the data travels the distance of the length of the local communication link. Link 365 can be implemented in a number of ways. Two examples are now described.

Figure 6:
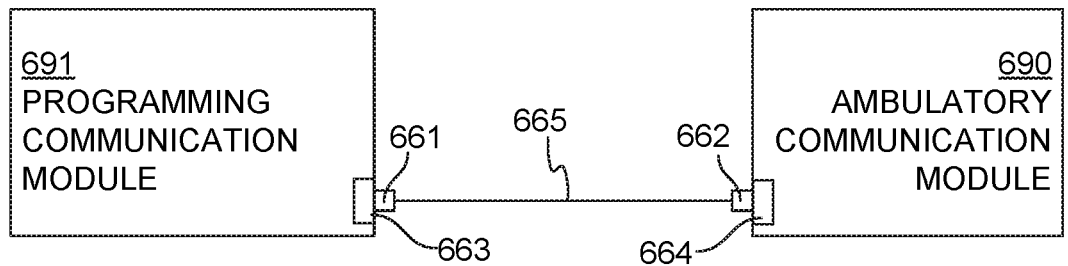
FIG. 6 is a diagram of sample components that could be used for the components of FIG. 3, in which a local communication link is at least partially established by a cable according to embodiments.

FIG. 6 shows a sample programming communication module 691 and a sample ambulatory communication module 690, which could be used for programming communication module 391 and ambulatory communication module 390, respectively. A local communication link is at least partially established by a cable 665, which terminates in plugs 661, 662. Programming communication module 691 has a socket 663 that plug 661 is plugged into, and ambulatory communication module 690 has a socket 664 that plug 662 is plugged into. Plugs 661, 662 and sockets 663, 664 may be USB or equivalent.

Figure 7:
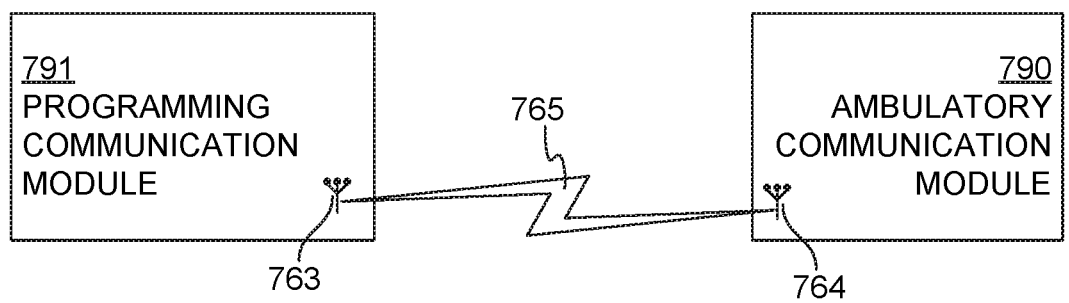
FIG. 7 is a diagram of sample components that could be used for the components of FIG. 3, in which a local communication link is wireless according to embodiments.

FIG. 7 shows a sample programming communication module 791 and a sample ambulatory communication module 790, which could be used for programming communication module 391 and ambulatory communication module 390, respectively. Programming communication module 791 has an antenna 763, and ambulatory communication module 790 has a an antenna 764. A wireless local communication link 765 is established by antennas 763 and 764. Wireless local communication link 765 can be by Bluetooth or other wireless equivalent. Pairing may have happened between programming communication module 791 and ambulatory communication module 790.

Returning to FIG. 3, in some embodiments, ambulatory user interface 380 outputs a human-visible indication 384, and programming screen 383 is configured to reproduce, in real time, the human-visible indication. This means that programming screen 383 may show an image that reproduces the human-visible indication. This has the advantage of facilitating the work of person 389 who is looking at programming screen 383 anyway while programming, but need not be looking concurrently at ambulatory user interface 380 so as to ascertain what it indicates and when. This is an advantage because looking also at ambulatory user interface 380 may be more problematic for person 389 if patient 382 is to stand up, sit down, walk or run on a treadmill, etc., all of which may take place during programming so as to receive a broad set of initial patient data.

In particular, in some embodiments ambulatory communication module 390 is configured to transmit defibrillator data over local communication link 365. This defibrillator data may be related to human-visible indication 384. In such embodiments, programming communication module 391 may be configured to receive, over local communication link 365, the defibrillator data transmitted by ambulatory communication module 390. Moreover, programming processor 331 may be configured to cause programming screen 383 to display a diagnostic image about human-visible indication 384, responsive to the defibrillator data received by programming communication module 391. Examples are now described.

Figure 8:
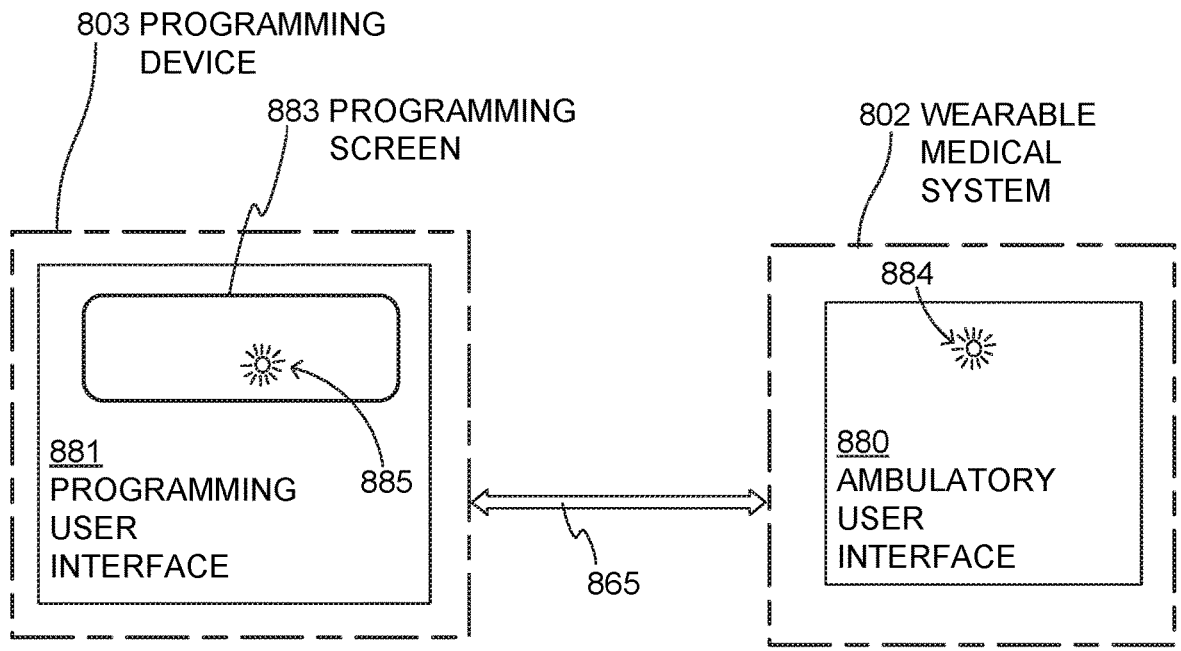
FIG. 8 is a diagram of salient portions of sample components that could be used for the components of FIG. 3, in which a sample ambulatory user interface outputs a human-visible indication, and a programming user interface has a programming screen displaying an image that reproduces the human-visible indication, according to embodiments.

FIG. 8 shows a WMS 802 with an ambulatory user interface 880, and a programming device 803 with a programming user interface 881. Programming device 803 may be used for programming WMS 802 over a link 865 similar to link 365.

Ambulatory user interface 880 is outputting a human-visible indication 884. Programming user interface has a programming screen 883 that is displaying a diagnostic image 885 about human-visible indication 884. In this embodiment, diagnostic image 885 reproduces human-visible indication 884, although that is not required for embodiments.

In some embodiments, diagnostic image 885 is displayed concurrently with human-visible indication 884 being output. This may be, technically speaking, redundant but still useful to either person 398 or patient 382 or both, for purposes of developing confidence as per the above. In some embodiments, controls may be used to turn off human-visible indication 884 during programming, i.e. while diagnostic image 885 is being displayed.

In some embodiments, the ambulatory user interface includes a light source, such as an LED. The light source may be configured to be turned on to output the human-visible indication, and then off. For instance, this could be the situation of FIG. 8, where human-visible indication 884 is the fact that a light source is lit. In such embodiments, the diagnostic image may depict the light source, as again could be the situation of FIG. 8. In fact, in some of these embodiments the light source can be thus turned on and off according to a certain pattern, and the diagnostic image may further depict the light source turning on and off according to the certain pattern.

In fact, in some embodiments, the WMS may include a surface, and the light source is on the surface. For example, the surface may be the surface of a housing or casing, the surface of a dongle connected by a cable to another device of the WMS, and so on. In such embodiments, the diagnostic image may further depict at least a portion of the surface. An example is now described.

Figure 9:
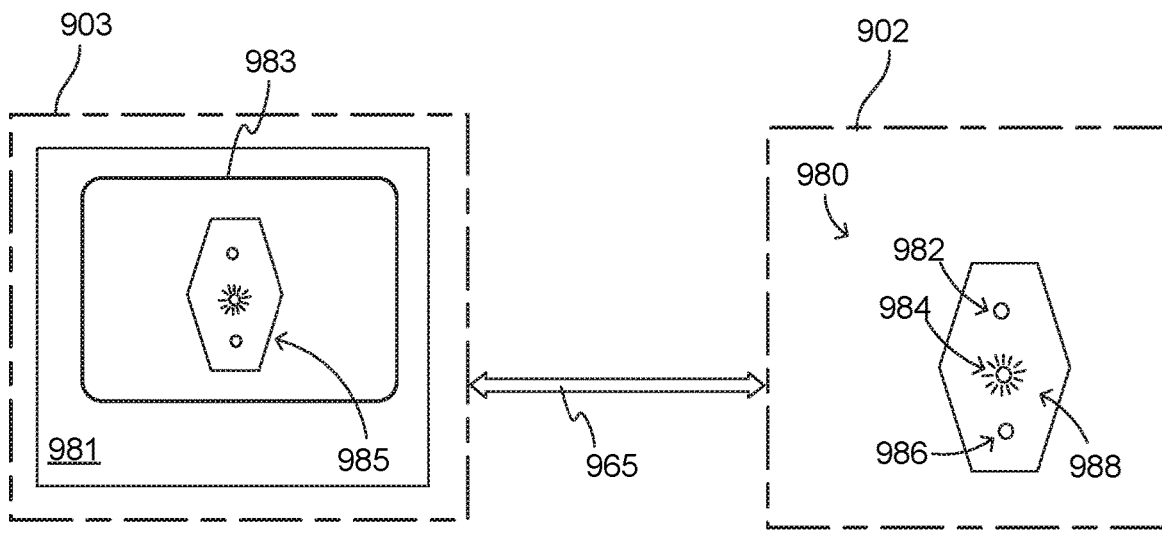
FIG. 9 is a diagram of salient portions of sample components that could be used for the components of FIG. 3, in which a sample ambulatory user interface has, on a surface, a light source that outputs a human-visible indication, and a programming user interface has a programming screen displaying an image that reproduces the surface and the human-visible indication, according to embodiments.

FIG. 9 shows a WMS 902 with an ambulatory user interface 980, and a programming device 903 with a programming user interface 981. Programming device 903 may be used for programming WMS 902 over a link 965 similar to link 365. Ambulatory user interface 980 includes a dongle 980, which is connected by a cable that is not shown so as to not clutter the drawing. Dongle 980 has three light sources 982, 984, 986 on a surface 988. A human-visible indication is being output by light source 984 being lit. Programming user interface 981 has a programming screen 983 that is displaying a diagnostic image 985. In this embodiment, diagnostic image 985 is an image of dongle 980, showing the surface and the light sources of dongle 980, and even with the corresponding light source shown as lit.

Returning to FIG. 3, in some embodiments, ambulatory user interface 380 includes an ambulatory screen. In such embodiments, human-visible indication 384 is displayed on the ambulatory screen, and the diagnostic image reproduces the human-visible indication. An example is now described.

Figure 10:
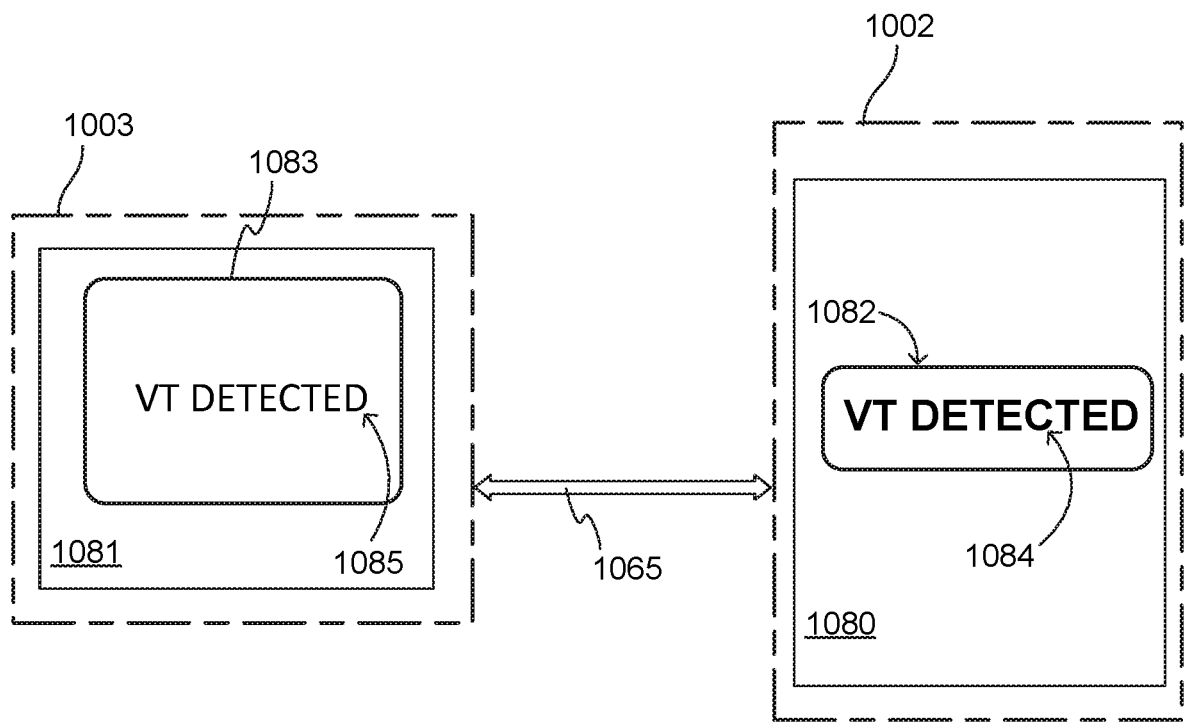
FIG. 10 is a diagram of salient portions of sample components that could be used for the components of FIG. 3, in which a sample ambulatory user interface has an ambulatory screen that outputs a human-visible indication, and a programming user interface has a programming screen that reproduces the human-visible indication, according to embodiments.

FIG. 10 shows a WMS 1002 with an ambulatory user interface 1080, and a programming device 1003 with a programming user interface 1081. Programming device 1003 may be used for programming WMS 1002 over a link 1065 similar to link 365. Ambulatory user interface 1080 includes has an ambulatory screen 1082.

A human-visible indication 1084 is displayed on ambulatory screen 1082. In this example, the human visible indication is a writing. In some embodiments, the human-visible indication is about the detection outcome and, when implemented by a writing, it serves as diagnosis. In embodiments, the detection outcome includes an asystole diagnosis, a bradycardia diagnosis, a supraventricular tachycardia (SVT) diagnosis, a ventricular tachycardia (VT) diagnosis, a ventricular fibrillation (VF) diagnosis, etc.

Programming user interface 1081 has a programming screen 1083 that is displaying a diagnostic image 1085. In this embodiment, diagnostic image 1085 reproduces human-visible indication 1084.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described, which may be performed by related described embodiments.

Figure 11:
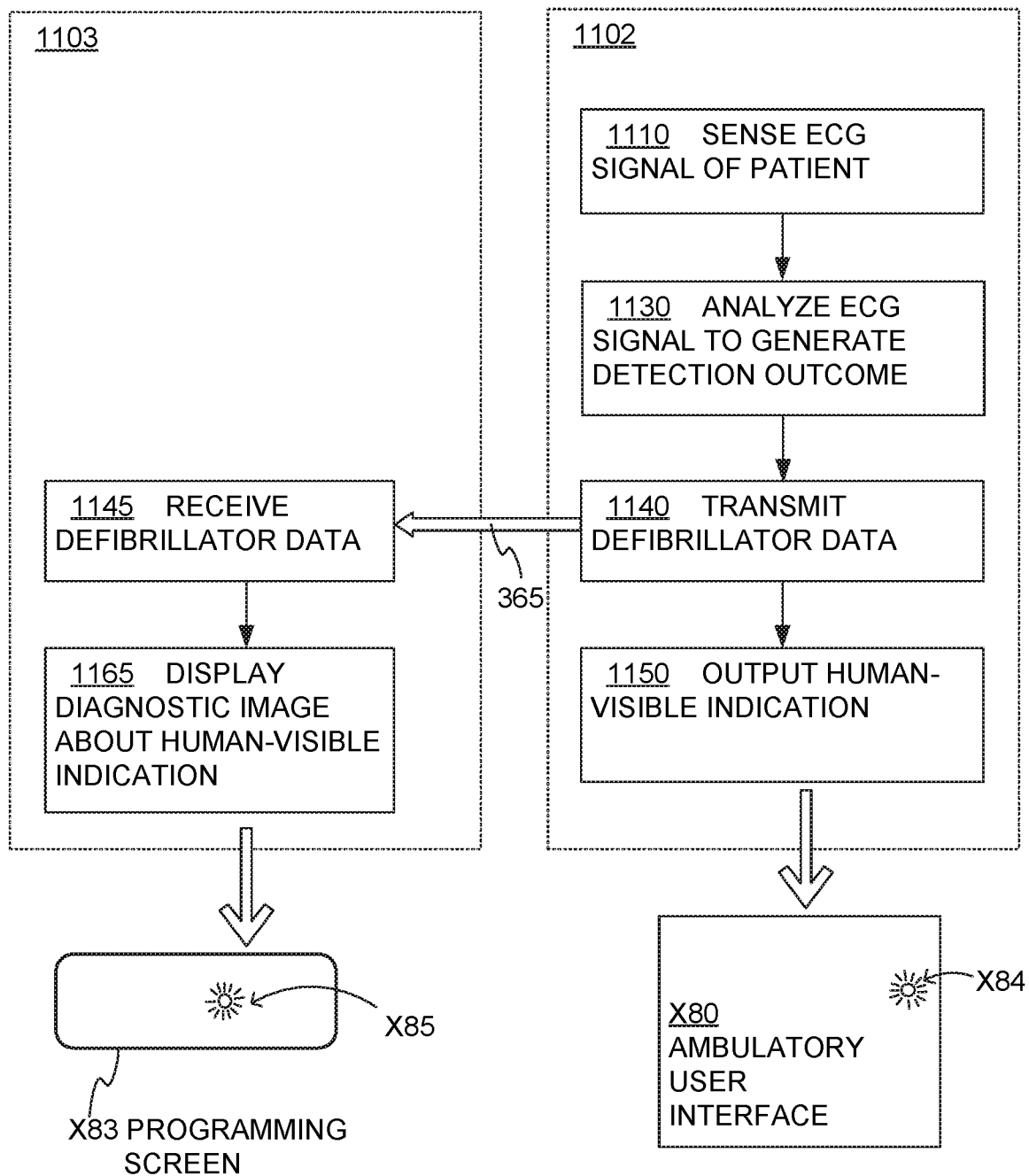
FIG. 11 is a diagram for illustrating methods according to embodiments.

FIG. 11 shows flowcharts 1103, 1102 for describing methods according to embodiments. Flowchart 1103 is used for illustrating operations being performed by programming device 303 of FIG. 3, while flowchart 1102 is used for illustrating operations being performed by wearable medical system 302, which could be a WCD system. These flowcharts 1103, 1102 are further annotated with elements that can be related to individual operations of the flowchart. In combinations according to embodiments, operations from both flowcharts may be performed.

According to an operation 1110 of flowchart 1102, an electrocardiogram (ECG) signal of a patient may be sensed, via at least some of the electrodes.

According to another operation 1130, the sensed ECG signal may be analyzed so as to generate a detection outcome from the sensed ECG signal. Analysis may be performed by an ambulatory processor of a wearable medical system.

According to another operation 1140, defibrillator data may be transmitted. The defibrillator data may be generated from the analysis of operation 1130, and be related to a human-visible indication X84. Transmitting may be performed by an ambulatory communication module of a wearable medical system, over local communication link 365.

According to another operation 1150, human-visible indication X84 may be output by an ambulatory user interface X80 of a wearable medical system. User interface X80 may be as written elsewhere in this document for other ambulatory user interfaces. Human-visible indication X84 may be as written above.

According to another operation 1145 of flowchart 1103, the defibrillator data transmitted at operation 1140 may be received by a programming communication module, for example over local communication link 365.

According to another operation 1165, a diagnostic image X85 may be displayed by programming screen X83, responsive to the defibrillator data received at operation 1145. Diagnostic image X85 may be about human-visible indication X84, and as written above.

Additional optional operations are possible. For example, an electrical charge may be discharged (411), by a defibrillator responsive to the detection outcome generated at operation 1130 through at least some of the electrodes 404, 408 while a support structure is worn by a patient, so as to deliver a shock to the patient.

Returning to FIG. 3, in some embodiments programming device 303 routinely stores and maintains stored ECG data that a wearable medical system (WMS), such as a wearable cardioverter defibrillator (WCD) system, normally discards after storing only briefly. Examples are now described.

Figure 12:
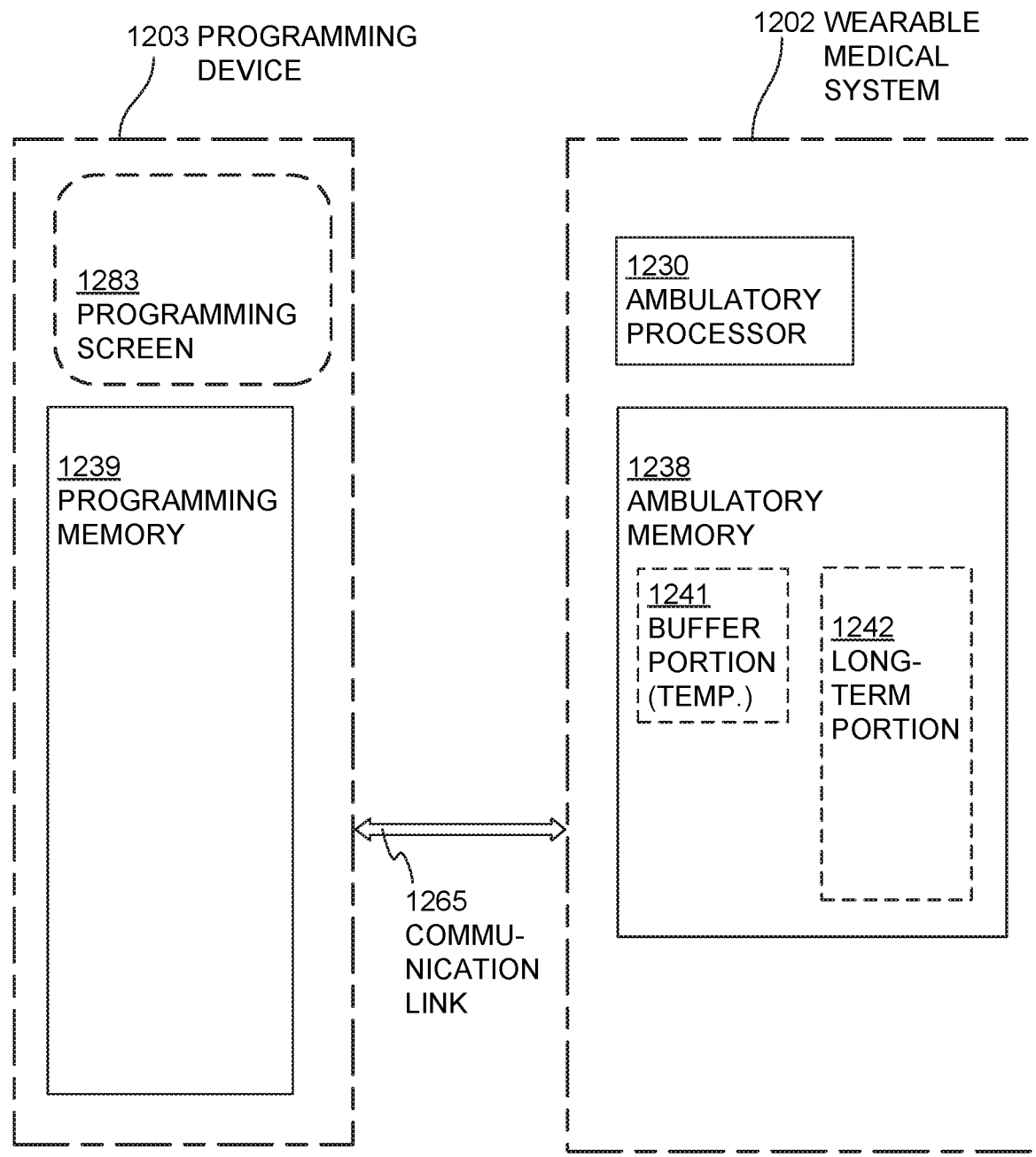
FIG. 12 is a diagram of salient portions of sample components that could be used for the components of FIG. 3, in which ECG data stored in a buffer portion of an ambulatory memory is regularly discarded after a brief buffer period, while the same data stored in the programming memory is maintained for a longer time than the buffer period, according to embodiments.

FIG. 12 shows a WMS 1202 and a programming device 1203, for describing some of the components of FIG. 3 in increasing detail. Programming device 1203 may be used for programming WMS 1202 over a link 1265 similar to link 365. Programming device 1203 has a programming memory 1239 and an optional programming screen 1283. WMS 1202 has an ambulatory processor 1230 an ambulatory memory 1238. Ambulatory memory 1238 includes a buffer portion 1241 and a long-term portion 1242. It will be understood that the different portions of memory 1238 may be implemented by different memory components, differently managed register addresses of a single memory component, and so on.

Sensed ECG data is stored initially in buffer portion 1241, but only temporarily. This data in buffer portion 1241 is then discarded after a brief buffer period, by being overwritten by newly-incoming sensed ECG data. In embodiments, sensed ECG data does become stored in long term portion 1242, but only if a detection outcome justifies it, for example if the sensed ECG data shows a starting heart arrhythmia that is worthy of monitoring because it could evolve into a treatable event, and so on. This is done to conserve memory space in WMS 1202. This is more important for a WMS that is also a WCD system, where there is no time to wait for treatment if an actionable event does happen.

Figure 13:
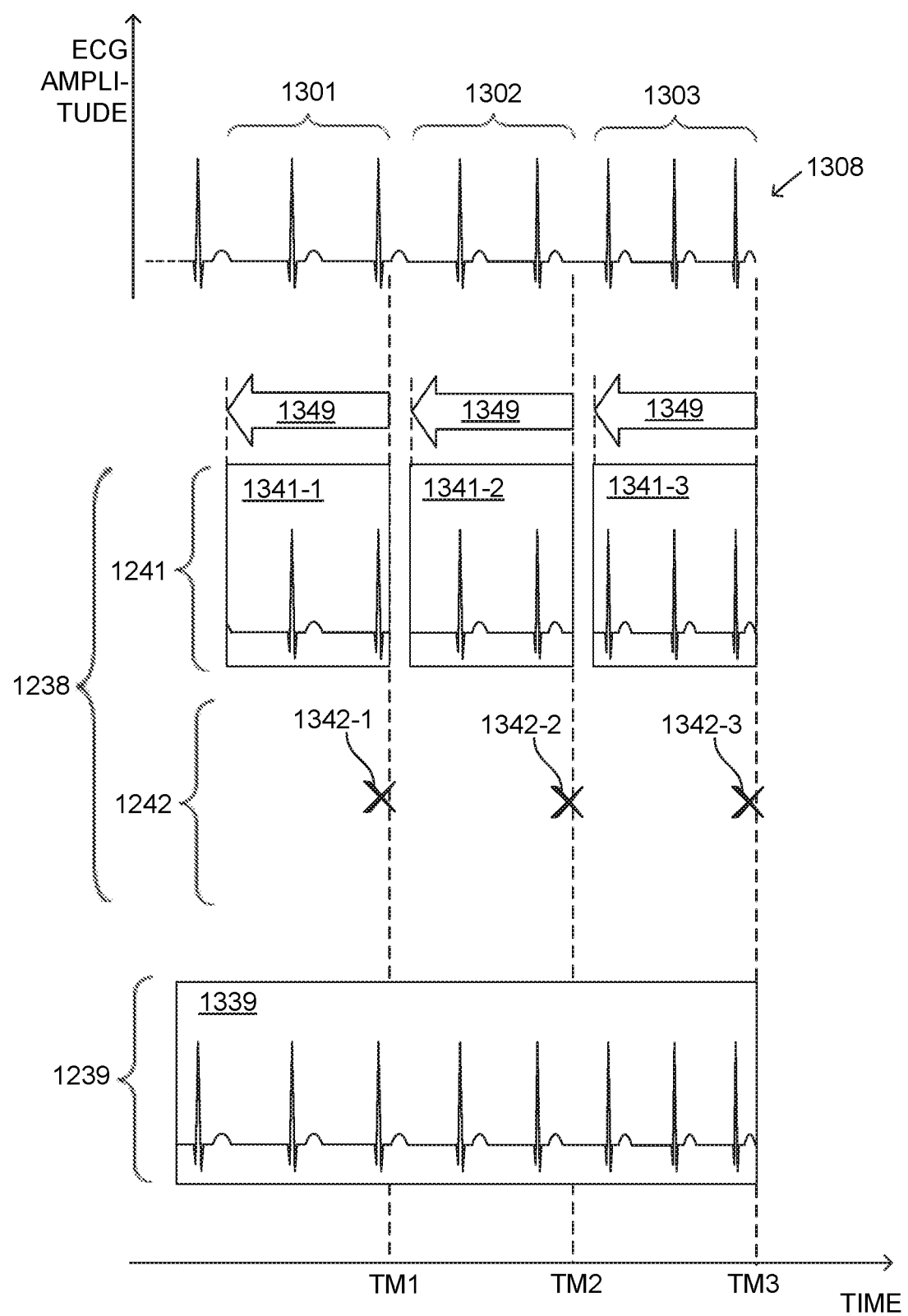
FIG. 13 is a group of time diagrams for illustrating an example of which ECG data is stored, in which memory, and for how long, according to embodiments.

For instance, referring to FIG. 13, an ECG signal 1308 could be sensed over a time period that spans at least three sample time intercepts TM1, TM2, TM3. For purposes of this example, ECG signal 1308 may have a first portion 1301, a subsequently sensed second portion 1302, and a subsequently sensed third portion 1303.

In embodiments, ambulatory processor 1230 can be configured to store in ambulatory memory 1238 first ECG data 1341-1 about first portion 1301. In such embodiments, this first ECG data 1341-1 may be stored in buffer portion 1241, and only for a buffer period BP 1349, shown as an arrow that looks backward in time for the most recent buffer period. As such, at time intercept TM1, buffer portion 1241 is storing this first ECG data 1341-1. Buffer period BP 1349 may have a duration of 30 seconds, 120 seconds, etc.

Ambulatory processor 1230 can be further configured to erase, after buffer period BP 1349, first ECG data 1341-1 from ambulatory memory 1238 by storing second ECG data 1341-2 over first ECG data 1341-1 in ambulatory memory 1238. As such, the erasing may be performed by overwriting with the more recently received second ECG data 1341-2. And, at time intercept TM2, buffer portion 1241 is storing this second ECG data 1341-2. Similarly, with continuing to over-write with the more recently received ECG data, at time intercept TM3, buffer portion 1241 is storing this third ECG data 1341-3.

In the example of FIG. 13, all ECG data written in ambulatory memory 1238 is over-written after buffer period BP 1349. In this example, no ECG data is remains stored or preserved for longer that time, and no ECG data is stored in long-term portion 1242. As such, at time intercepts TM1, TM2, TM3, respective null sets 1342-1, 1342-2, 1342-3 are stored in long-term portion 1242.

In such embodiments, ambulatory communication module 390 can be configured to transmit first ECG data 1341-1 over communication link 1265 or 365, and programming communication module 391 can be configured to receive first ECG data 1341-1 that was thus transmitted. Moreover, in such embodiments programming processor 331 can be configured to cause programming memory 1239 to store received first ECG data 1341-1 for a time at least twice as long as buffer period BP 1349, i.e. 2×BP, and preferably longer. This can be seen in FIG. 13, where ECG data 1339 is indicated as stored in programming memory 1239. In this example, ECG data 1339 includes not only first ECG data 1341-1, but all the ECG data that has been received by time intercept TM3. Of all that data, it will be appreciated that first ECG data 1341-1 has been preserved by remaining stored for at least two buffer periods 2×BP after time intercept TM1.

Figure 14:
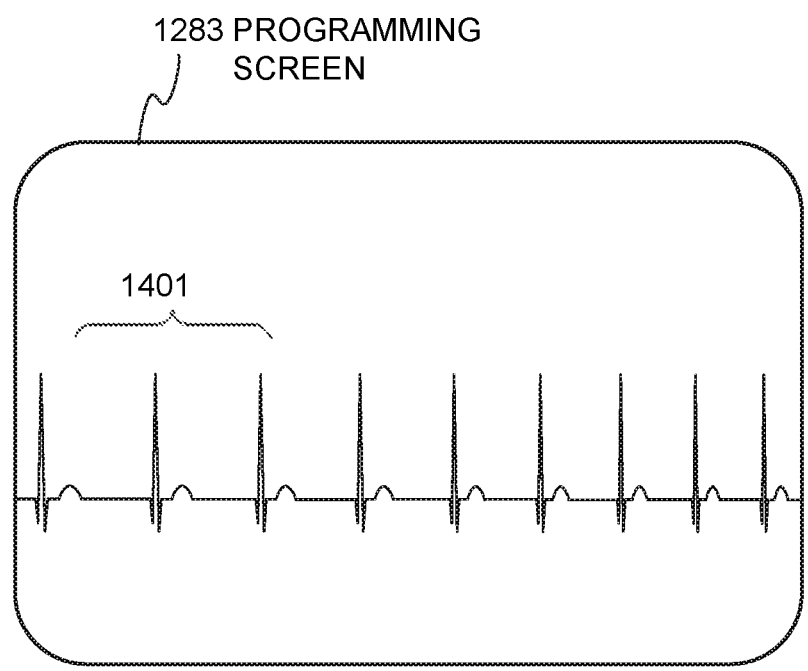
FIG. 14 is a diagram of a sample screenshot of a programming screen of FIG. 12 according to embodiments.

In embodiments, programming device 1203 further includes a programming screen 1283, which can be made as was described for programming screen 383. An example of that is seen in FIG. 14. Programming screen 1283 can be configured to display, after first ECG data 1341-1 has been thus erased from ambulatory memory 1238, an image 1401 of the first portion 1301 of the ECG signal, which is constructed from the received first ECG data 1341-1, plus additional ECG data sensed later.

The image of FIG. 14 can be thus analyzed long after first ECG data 1341-1 has been discarded by WMS 1202. This is a significant advantage, because it permits review of ECG data, and of detection outcomes of that ECG data that is not otherwise available, as WMS 1202 regularly discards ECG data and their detection outcomes if the latter do not indicate a possibly treatable event.

WMS 1202 regularly discards ECG data so as to conserve memory space. WMS 1202 may make a judgement as to when to start preserving the ECG data, instead of discarding it. An example is now described, which uses some of the same embodiments as above, and may occur later in time than the above.

Figure 15:
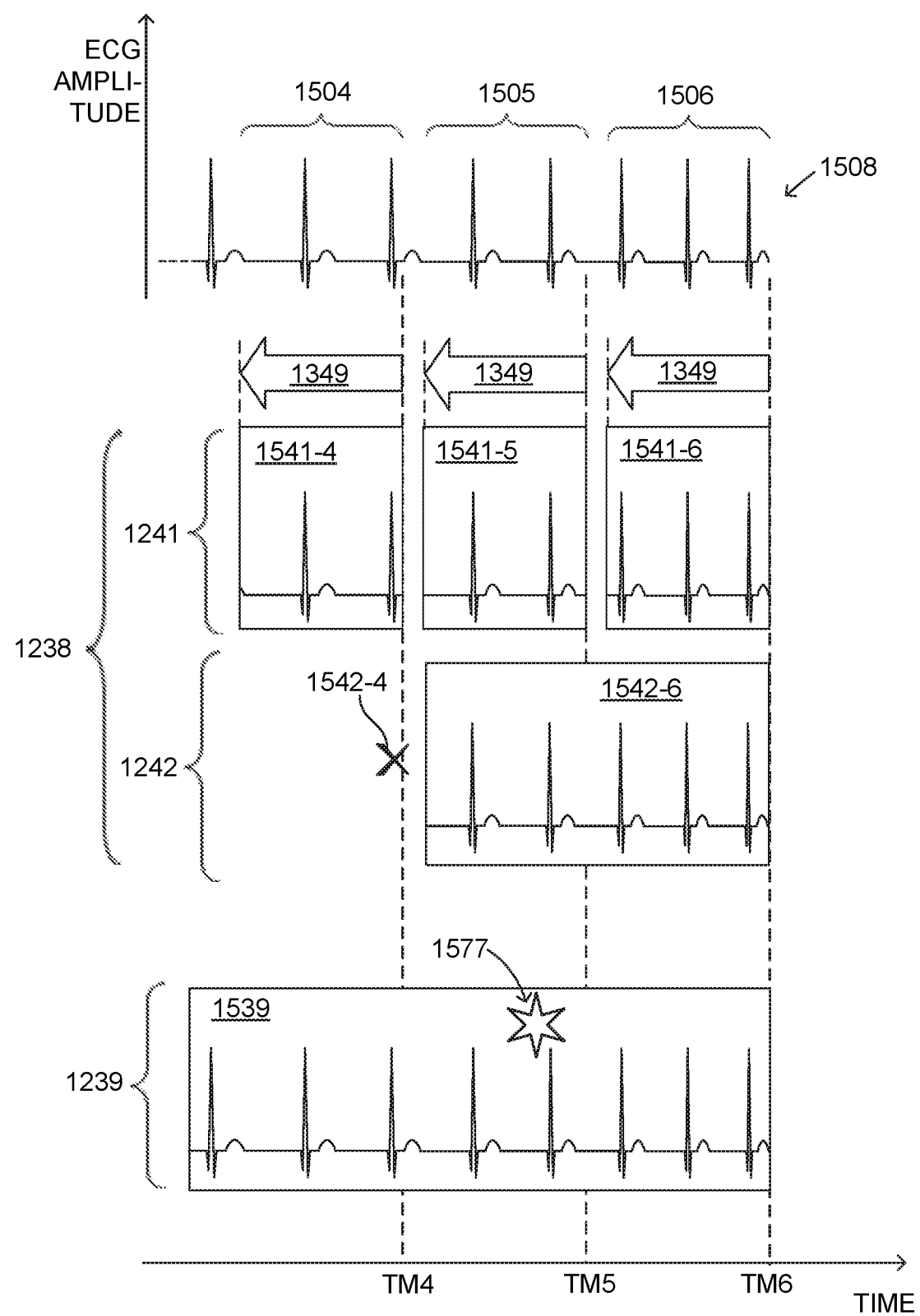
FIG. 15 is a group of time diagrams for illustrating another example of which ECG data is stored, in which memory, and for how long, according to embodiments.

For instance, referring to FIG. 15, an ECG signal 1508 could be sensed over a time period that spans at least three sample time intercepts TM4, TM5, TM6, all occurring after time intercept TM3. As previously, ECG signal 1508 may have a first portion 1504, a subsequently sensed second portion 1505, and a subsequently sensed third portion 1506.

In embodiments, as also previously, ambulatory processor 1230 can be configured to store in ambulatory memory 1238 first ECG data 1541-4 about first portion 1504, then over-write it with second ECG data 1541-5 about second portion 1505, and then over-write it with third ECG data 1541-6 about third portion 1506. As also previously these can be stored in buffer portion 1241. Plus, the ECG data may also be transmitted to programming device 1203, where it is stored in programming memory 1239 as data 1539 by time intercept TM6. And, by time intercept TM4, still nothing may be stored in long-term portion 1242, as indicated by a null set 1542-4.

Differently from FIG. 13, in FIG. 15 the detection outcome of ambulatory processor 1230 has a certain value at some time after time intercept TM4. This is denoted in FIG. 15 by an event marker 1577, which can be of a type that is described later in this document. In such embodiments, responsive to the detection outcome having a certain value, second ECG data 1541-5 can remain stored in ambulatory memory 1238 for a time longer than buffer period BP 1349, for later review. In the example of FIG. 15, this happens by starting to store the ECG data in long-term portion 1242. As such, at time intercept TM6, long-term portion 1242 stores not only second ECG data 1541-5, but also all the ECG data that has been received after it. Of that data, it will be appreciated that second ECG data 1541-5 has been preserved by remaining stored longer than buffer period BP 1349.

FIG. 15 exemplifies an advantage of this disclosure. ECG data is generated and maintained for the long term by WMS 1202 as data 1542-6 only if there is a reason for it, in other words, if the algorithm has been programmed to store it responsive to the detection outcome having a certain value. Other data 1341-1, 1341-2, 1341-3, 1541-4, however, is routinely discarded because the overall ambulatory memory 1238 is limited. And person 389 using the programming device does not otherwise have the opportunity to explore nuances in such other data, for instance when it indicates a mild bradycardia that may be adjusted differently for every person.

It is noteworthy that event marker 1577 was occasioned by the detection outcome of ambulatory processor 1230 having a certain value. in addition, in embodiments where WMS 1202 is a WCD system, the included defibrillator can be configured to deliver a shock the patient responsive to the detection outcome having a particular value. That particular value can be the same as, or different than, the certain value that gave rise to event marker 1577 and the starting of recording.

As will be seen in more detail later, event marker 1577 is of a type that can be called "open episode". An WMS may designate a sequence of events as an episode worthy of recording. An open episode decision may be later followed by a close episode decision, which can stop the long term recording, and so on.

Additional methods are now described, which may be performed by related described embodiments.

FIG. 16 shows flowcharts 1603, 1602 for describing methods according to embodiments. Flowchart 1603 is used for illustrating operations being performed by programming device 303 or 1203, while flowchart 1602 is used for illustrating operations being performed by wearable medical system 302 or 1202, which could be a WCD system. In combinations according to embodiments, operations from both flowcharts may be performed.

According to an operation 1610 of flowchart 1602, an electrocardiogram (ECG) signal of a patient may be sensed, via at least some of the electrodes.

According to another operation 1620, first ECG data 1341-1 about a first portion of the ECG signal may be stored.

According to another operation 1630, the sensed ECG signal may be analyzed so as to generate a detection outcome from the sensed ECG signal. Analysis may be performed by an ambulatory processor of a wearable medical system.

According to another operation 1640, the first ECG data may be transmitted. Transmitting may be performed by an ambulatory communication module of a wearable medical system, over a link 1665 similar to link 365.

According to another operation 1660, the first ECG data may be erased from the ambulatory memory after a buffer period BP 1349 after having stored it. Erasing may be performed by storing second ECG data 1341-2 over first ECG data 1341-1.

According to another operation 1645 of flowchart 1603, first ECG data 1341-1 transmitted at operation 1640 may be received by a programming communication module, over link 1665.

According to another operation 1655, first ECG data1341-1 received at operation 1645 may be stored in a programming memory for a time at least twice as long as buffer period BP 1349.

According to another, optional operation 1665, an image of the first portion of the ECG signal may be displayed on a programming screen after the first ECG data has been thus erased from the ambulatory memory, the displayed image having been constructed from the received first ECG data.

Additional optional operations are possible. For example, the second ECG data, such as 1545-5, may be stored in the ambulatory memory for a time longer than the buffer period BP, responsive to the detection outcome having a certain value. In other words, the cycle of routinely discarding ECG data after storing it for the buffer period BP may be broken.

For another example, an electrical charge may be discharged (411) by a defibrillator through a patient, responsive to the detection outcome generated at operation 1630 having a particular value, so as to deliver a shock to the patient.

Returning to FIG. 3, in some embodiments programming device 303 is used to program in real time a wearable medical system (WMS), which could be a wearable cardioverter defibrillator (WCD) system, so as to customize the WMS for a patient. Examples are now described.

Figure 17A:
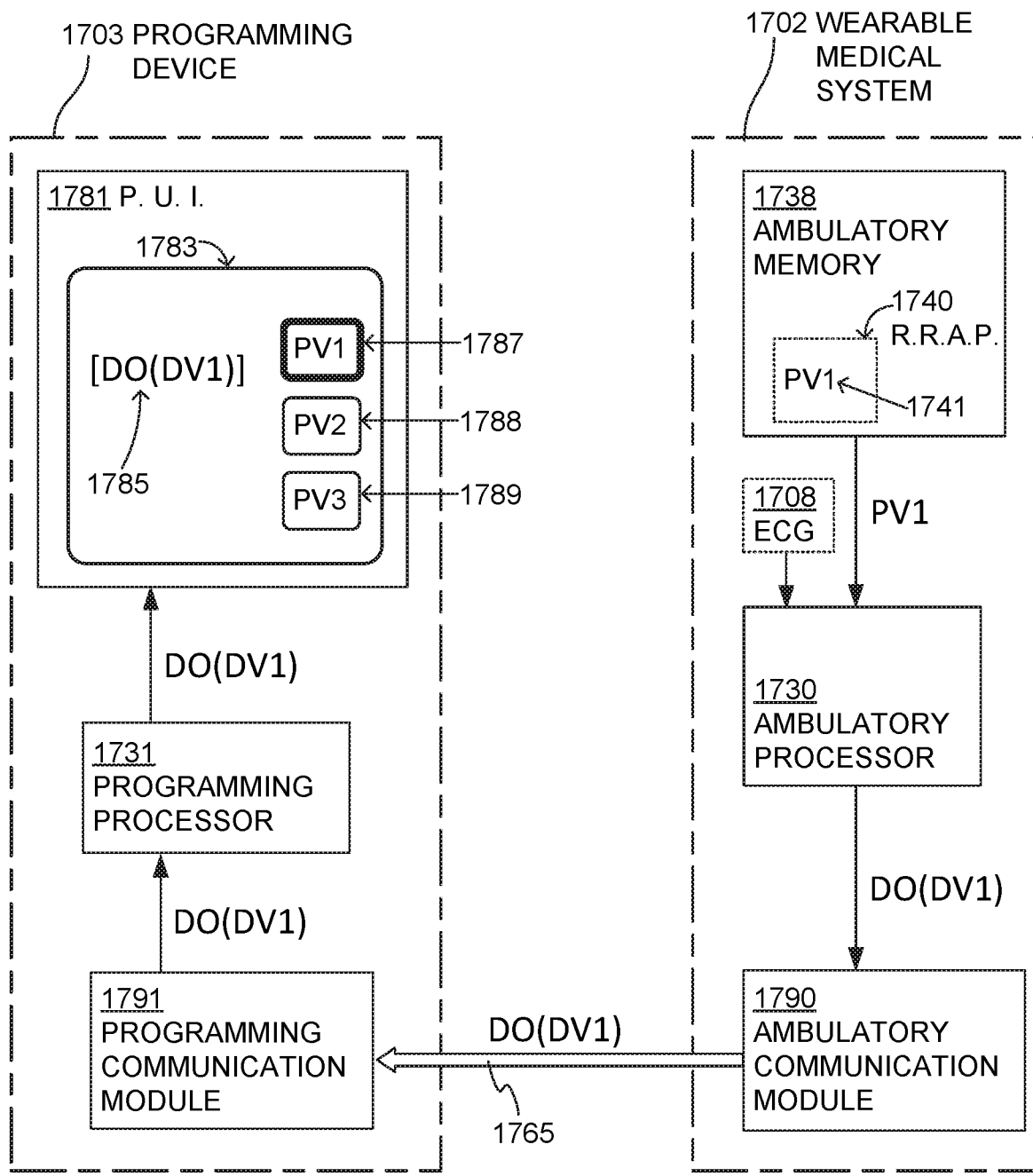
FIGS. 17A-17C are diagrams showing sample successive detailed snapshots of salient components that could be used for the components of FIG. 3, in which a person using a programming device may view different detection values generated based on programming different parameter values in real time for a single patient in a wearable medical system, according to embodiments.
Figure 17B:
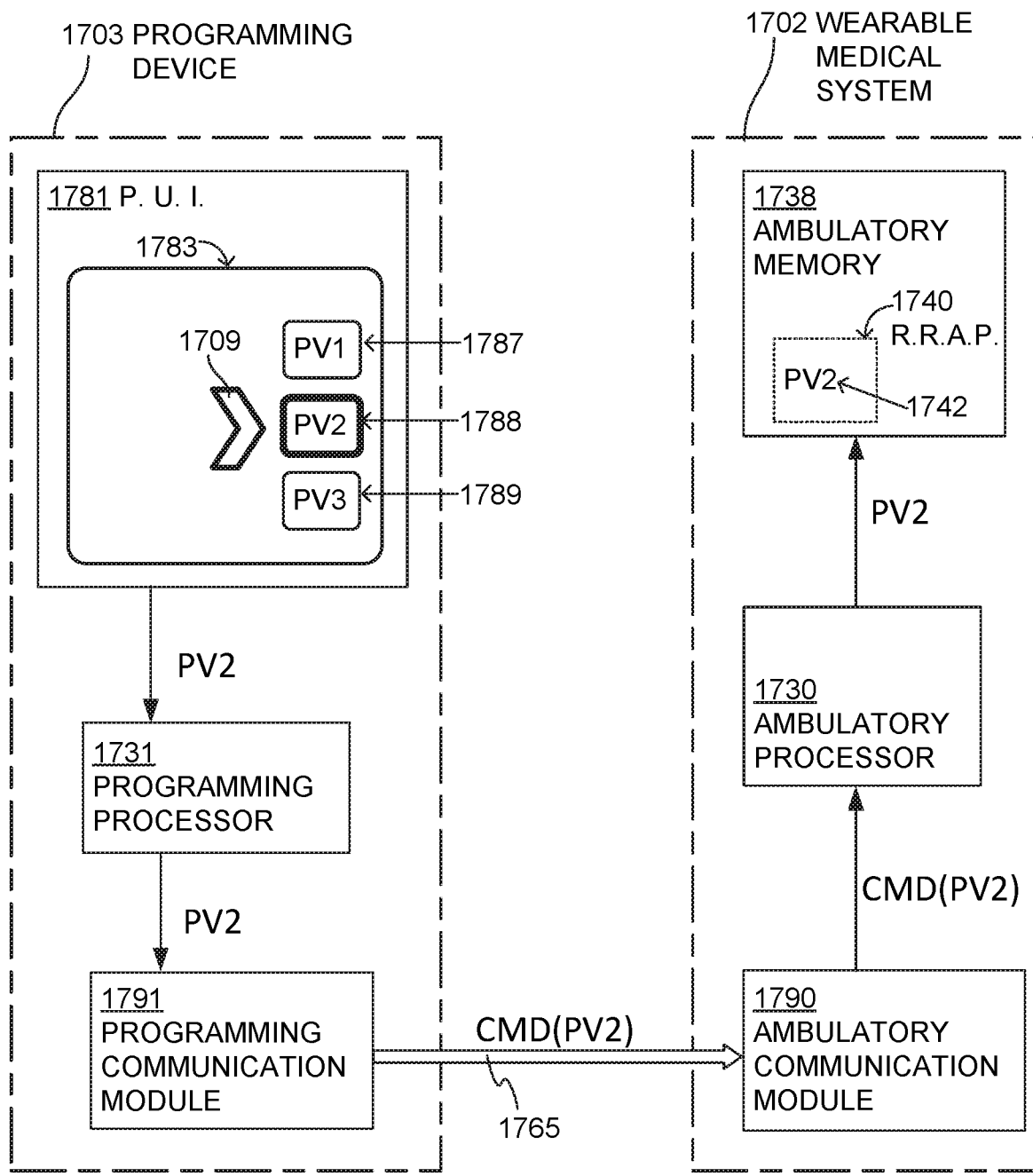
Figure 17C:
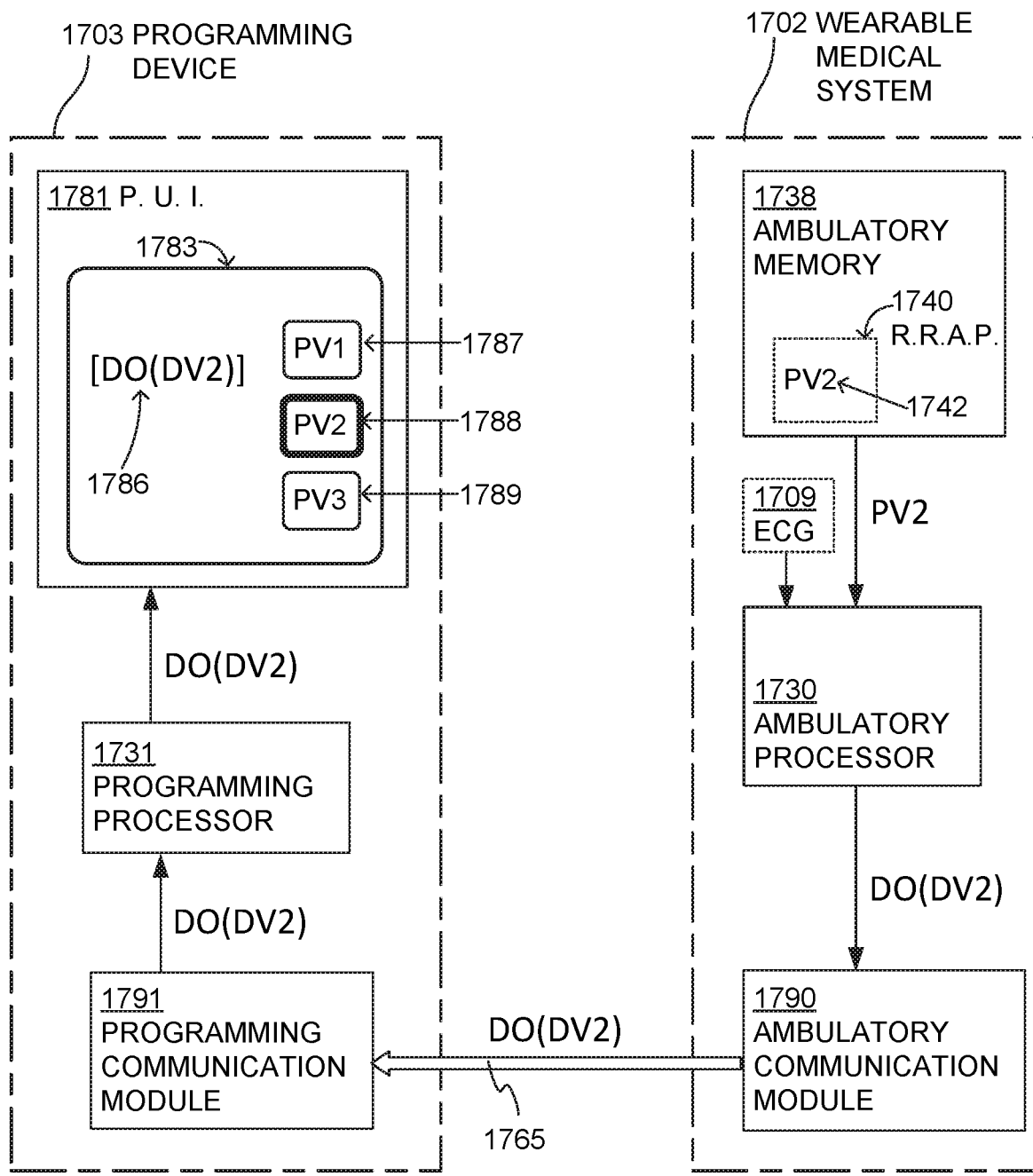

FIGS. 17A-17C show a WMS 1702 and a programming device 1703, for describing some of the components of FIG. 3 in greater detail as successive snapshots. Programming device 1703 may be used for programming WMS 1702 over a link 1765 similar to link 365.

Programming device 1703 includes a programming communication module 1791, a programming processor 1731, and a programming user interface 1781 that includes a programming screen 1783. Programming user interface 1781 is also configured to receive user inputs entered by person 389.

WMS 1702 includes an ambulatory memory 1738 that is configured to store a parameter value as a rhythm analysis parameter. Programming by programming device 1703 may update this stored parameter value. In some embodiments, ambulatory memory 1738 includes one or more registers 1740 for storing the value of the rhythm analysis parameter, and for looking up that value when needed for the analysis.

WMS 1702 also includes an ambulatory processor 1730. Ambulatory processor 1730 can be configured analyze ECG signals, such as an ECG signal 1708 or an ECG signal 1709, subject to the parameter value that is stored as the rhythm analysis parameter in ambulatory memory 1738. WMS 1702 further includes an ambulatory communication module 1790, which can exchange data with programming communication module 1791 over link 1765.

An example is now described where person 389 uses programming device 303 or 1703 to program WMS 302 or 1702. Referring first to FIG. 17A, ambulatory memory 1738 stores, as the rhythm analysis parameter, a first parameter value PV1 1741.

Then, ambulatory processor 1730 may analyze, subject to parameter value PV1 1741 that is currently stored as the rhythm analysis parameter, sensed ECG signal 1708, so as to generate a detection outcome DO from the sensed ECG signal. The detection outcome DO has a first detection value DV1, due to the first parameter value PV1 1741 being thus stored as the rhythm analysis parameter. This detection outcome that has the first detection value DV1 can also be written as DO(DV1).

Then ambulatory communication module 1790 may transmit the detection outcome DO(DV1) over local communication link 1765. In turn, programming communication module 1791 may receive, over local communication link 1765, detection outcome DO(DV1) that was transmitted by ambulatory communication module 1790.

Then programming screen 1783 may display, as a diagnostic image 1785, the received detection outcome DO(DV1) for person 389 to view.

In some embodiments, programming screen 1783 is configured to further display, for person 389 to view, the first parameter value PV1 1741 that was used as the rhythm analysis parameter for generating the displayed detection outcome DO(DV1). In this example, programming screen 1783 further displays first parameter value PV1 as a button 1787. This way, the displayed value of PV1 can be mentally associated by person 389 with the displayed detection outcome DO(DV1).

In some of these embodiments, programming screen 1783 is configured to further display, for person 389 to view, also another parameter value, such as a second parameter value, even though that second parameter value was not used. In this example, programming screen 1783 further displays a second possible parameter value PV2 as another button 1788. Second parameter value PV2 can be different from first parameter value PV1. Since second parameter value PV2 is not the one used for the displayed detection outcome DO(DV1), its button 1788 is preferably shown less prominently than button 1787. In this example, button 1787 is shown with an illuminated perimeter. In this example, programming screen 1783 further displays a third possible parameter value PV3 as one more button 1789.

Referring next to FIG. 17B, programming user interface 1781 is configured to then receive from person 389 a programming input, after programming screen 1783 thus displays the received detection outcome seen in FIG. 17A. The programming input may be about ambulatory processor 1730 transitioning to using second parameter value PV2 instead of first parameter value PV1 as the rhythm analysis parameter. For example, the programming input can be a command about using second parameter value PV2 instead of first parameter value PV1. In this example, the programming input is indicated as an icon 1709, which is intended to indicate that person 389 pushes button 1788.

In such embodiments, programming processor 1731 can be configured to cause programming communication module 1791 to transmit, responsive to the received programming input, a command CMD(PV2) in furtherance of the programming input over link 1765. Moreover, ambulatory communication module 1790 can be further configured to receive command CMD(PV2) that was thus transmitted by programming communication module 1791.

In such embodiments, ambulatory processor 1730 can be further configured to then store, responsive to transmitted command CMD(PV2), in ambulatory memory 1738 second parameter value PV2 in lieu of first parameter value PV1 as the rhythm analysis parameter.

In such embodiments, ambulatory memory 1738 can be configured to store, as the rhythm analysis parameter, second parameter value PV2 instead of first parameter value PV1. In this example, this is indicated as value PV2 1742 being now stored in the one or more registers 1740.

Referring next to FIG. 17C, ambulatory processor 1730 can be further configured to analyze, subject to the updated second parameter value that is stored as the rhythm analysis parameter, a sensed ECG signal 1709 so as to generate a detection outcome that has a second detection value DO(DV2). Second detection value DO(DV2) may be different from first detection value DO(DV1), due to second parameter value PV2 being thus stored as the rhythm analysis parameter instead of first parameter value PV1.

Then, similarly with FIG. 17A, ambulatory communication module 1790 may transmit the detection outcome DO(DV2) over local communication link 1765, where it may be received by programming communication module 1791. Then programming screen 1783 may display, as a diagnostic image 1786, the received detection outcome DO(DV2) for person 389 to view.

In this example, differently designated ECG signals 1708, 1709 were used. In embodiments, the ECG signals may be different, or different portions of the same ECG signal. In some embodiments, however, a single portion of the ECG signal may be analyzed with first parameter value PV1 as the rhythm analysis parameter, as shown in FIG. 17A, and that single portion of the ECG signal can be stored in ambulatory memory 1738 and then analyzed again with second parameter value PV2 as the rhythm analysis parameter, as shown in FIG. 17C.

FIGS. 17A-17C showed only a few elements of what a programming screen could display. A more detailed example is now provided according to embodiments.

Figure 18:
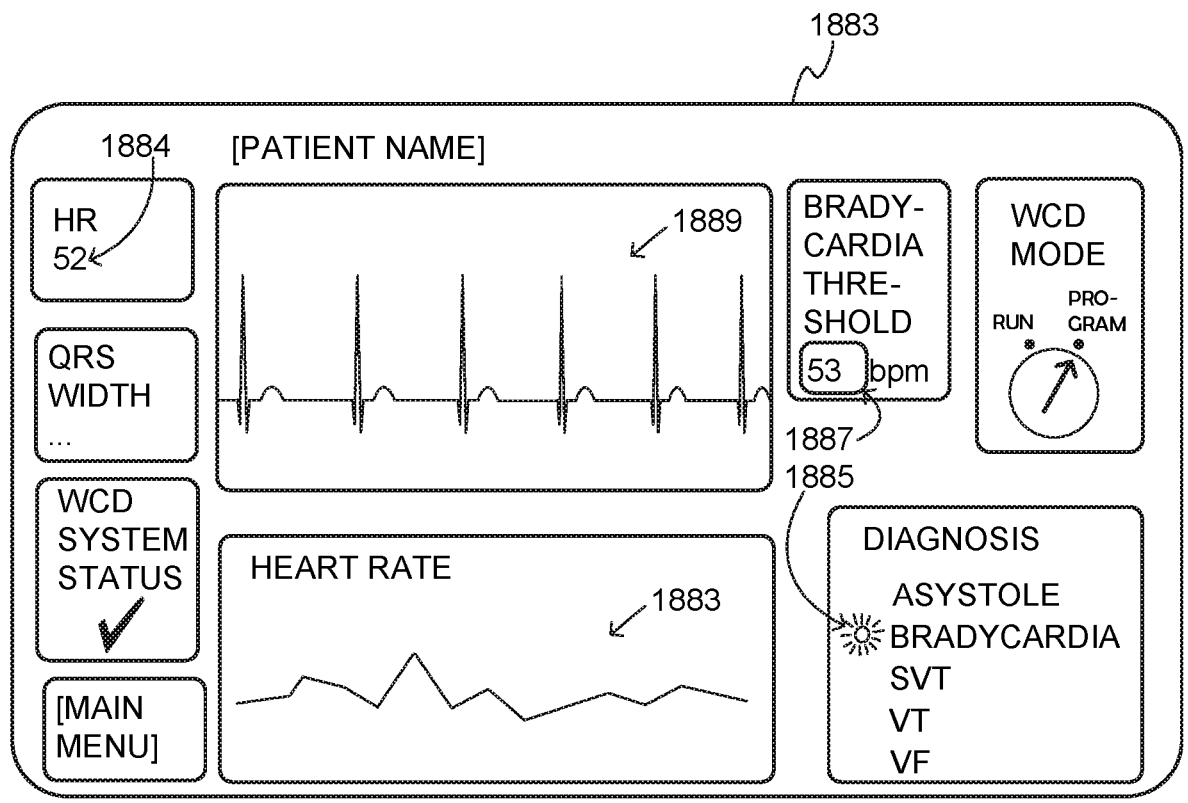
FIG. 18 is a diagram of a sample programming screen of a programming user interface made according to embodiments.

FIG. 18 is a diagram of a sample programming screen 1883. Programming screen 1883 may be a touchscreen, and has a number of sections.

In some embodiments, the ambulatory communication module 1790 is further configured to transmit, over local communication link 1765, ECG data about the sensed ECG signal. In such embodiments, programming communication module 1791 can be further configured to receive the thus transmitted ECG data, and programming screen 1783 can be further configured to display an image of the sensed ECG signal that is constructed from the received ECG data. In the example of FIG. 18, an image 1889 of the sensed ECG signal is constructed and displayed in programming screen 1883.

In some embodiments, ambulatory processor 1730 is further configured to extract a rhythm statistic from the sensed ECG signal. The rhythm statistic may include, for example, a heart rate, a QRS width, etc. In such embodiments, ambulatory communication module 1790 can be further configured to transmit the rhythm statistic, and programming screen 1783 can be further configured to display an image of the transmitted rhythm statistic. In the example of FIG. 18, an image 1883 of a time history of the extracted heart rate is displayed in programming screen 1883, while an instantaneous value 1884 is also displayed.

In some embodiments, first parameter value PV1 represents a heart rate threshold. In such embodiments, the first detection value DV1 of detection outcome DO indicates a determination that a heart rate extracted from the sensed ECG signal exceeds the heart rate threshold. In the example of FIG. 18, first parameter value PV1 represents a heart rate threshold for bradycardia, and is indicated by a button 1887 as 53 beats per minute (bpm). In this example, since current rate is 52 bpm, the heart rate threshold for bradycardia is exceeded, in the negative direction of course. As such, the first detection value DV1 of detection outcome DO is that bradycardia is detected, and is indicated by a diagnostic image 1885.

Here, in the programming stage, if hypothetically person 389 programs the WMS to transition to using a second parameter value PV2 of 51 bpm instead of the first parameter value PV1 of 53 bpm, then the detection outcome would have a different detection value DV2: no bradycardia detected. Person 389 may make such a judgement upon personally observing patient 382, and so on. And it will be recognized that this was an example of how bradycardia is defined; equivalently, other diagnoses could be defined, such as asystole, supraventricular tachycardia (SVT), ventricular tachycardia (VT), and ventricular fibrillation (VF).

Similarly, in some embodiments, first parameter value PV1 represents a QRS width threshold. In such embodiments, the first detection value DV1 of detection outcome DO indicates a determination that a QRS width extracted from the sensed ECG signal exceeds the QRS width threshold.

In some embodiments, the programming screen is configured to display the detection outcome as an event marker icon. Examples are now described.

Figure 19A:
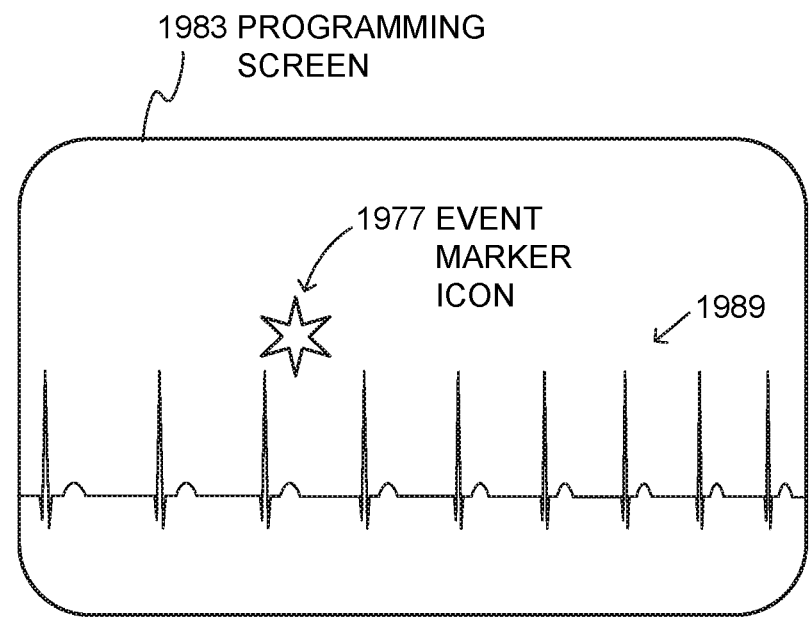
FIG. 19A is a diagram of a sample programming screen, in which an event marker icon is displayed along with ECG data according to embodiments.

FIG. 19A shows a sample programming screen 1983. As with FIG. 18, in FIG. 19A the ECG signal 1989 is displayed. An event marker icon 1977 is also displayed at a place relative to the displayed ECG signal 1989 that indicates when the detection outcome was made relative to the ECG signal.

An event marker icon may be displayed due to a variety of reasons according to embodiments. For example, an event marker icon is about a diagnosis of the patient made by the WMS. For another example, the event marker icon is about a decision made by the WMS, for instance to open or close an episode to change state, to deliver a shock, and so on.

For example, for opening an episode, a sample event marker 1577 was seen in FIG. 15, but that was a marker stored in a memory, not an icon displayed for person 389. Such can also be displayed. For example, according to embodiments, first ECG data can be stored in the ambulatory memory about a first portion of the ECG signal and then, after buffer period BP, the first ECG data can be erased from the ambulatory memory by storing second ECG data over the first ECG data in the ambulatory memory. If, however, the first detection value of the detection outcome indicates that an open episode decision is made in order to start preserving portions of the ECG signal for a time longer than buffer period BP then, responsive to the open episode decision being made, the second ECG data does not become erased after buffer period BP similarly to how the first ECG data was erased, but the second ECG data may remain stored in the ambulatory memory for at least twice as long as the buffer period BP. An example of that recording activity was seen in FIG. 15. Plus, this can be followed by a close episode decision that is indicated by a close episode marker, and so on.

In embodiments where the detection outcome is displayed as an event marker icon, the programming user interface may be configured to receive from person 389 an activation input about the displayed event marker icon, and the programming screen can be configured to further display determinative data that was used to generate the detection outcome, responsive to the received activation input. An example is are now described.

Figure 19B:
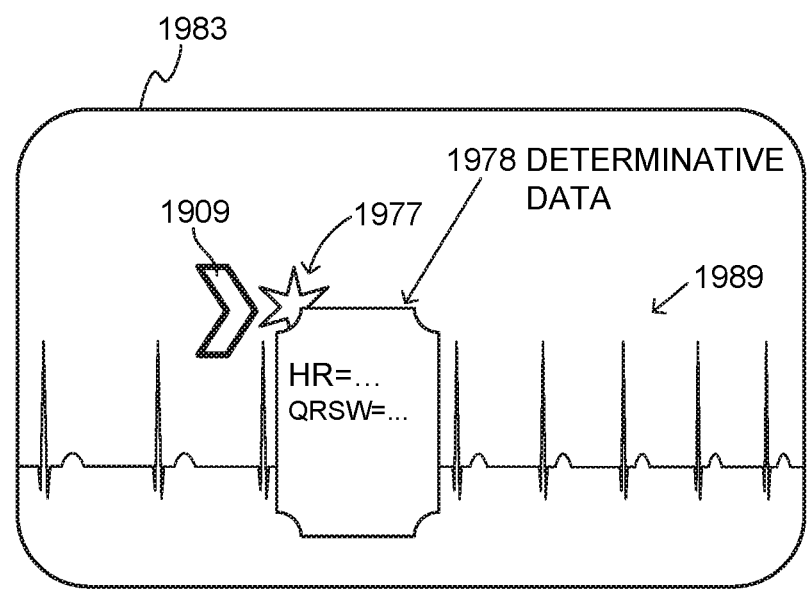
FIG. 19B is a diagram of the programming screen of FIG. 19A, in which the event marker icon has been activated to further display sample determinative data according to embodiments.

FIG. 19B shows sample programming screen 1983 of FIG. 19A. In addition, an activation input 1909 about displayed event marker icon 1977 is received. Such an activation input 1909 can be, for example by clicking on or hovering over event marker icon 1977, touching it in a touchscreen, and so on. In some of these embodiments, such event marker icons operate as hyperlinks. As such, event marker icon 1977 has been activated to further display sample determinative data 1978 according to embodiments. In this case, determinative data 1978 can be a combination of heart rate and QRS width that exceeded a threshold. In other instances, the determinative data can be what parameters gave rise to a diagnosis, to a decision, etc. For example, a decision can be to deliver a defibrillation shock to the patient, etc.

Figure 20:
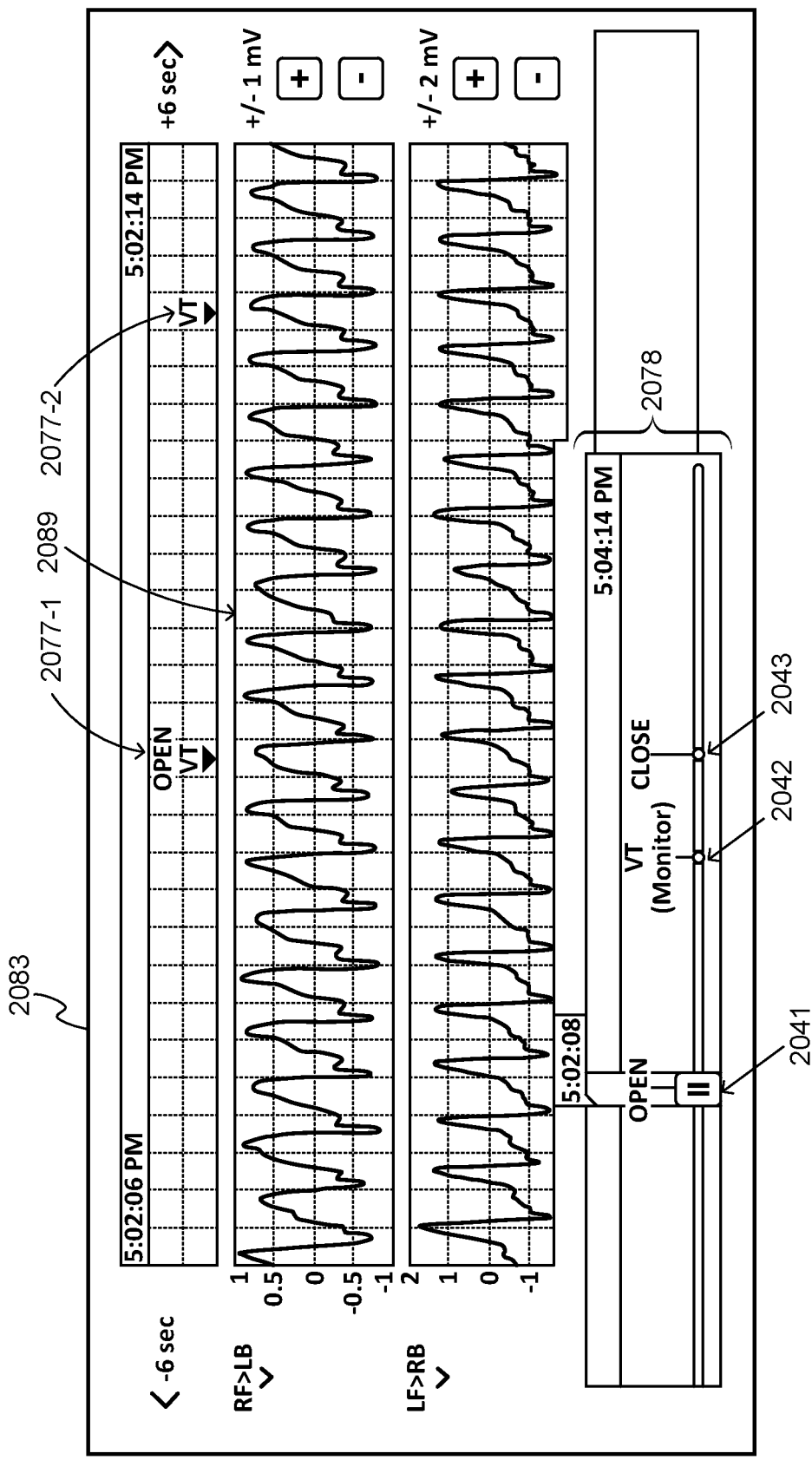
FIG. 20 is a screenshot of another sample programming screen in which event marker icons are displayed along with ECG data and determinative data according to embodiments.

FIG. 20 shows another sample programming screen 2083. An ECG signal 2089 is displayed, along with values for time and also two event data markers 2077-1, 2077-2. Upon activation with an activation input, determinative data 2078 is shown of events where: an episode was opened (2041), VT was monitored for (2042), and when the episode was closed (2043). Moreover, this determinative data may again be shown as icons, or even hyperlinks that can be activated for embedding further information hierarchically so as to conserve space on the screen, and so on.

Further methods are now described, which may be performed by related described embodiments.

Figure 21:
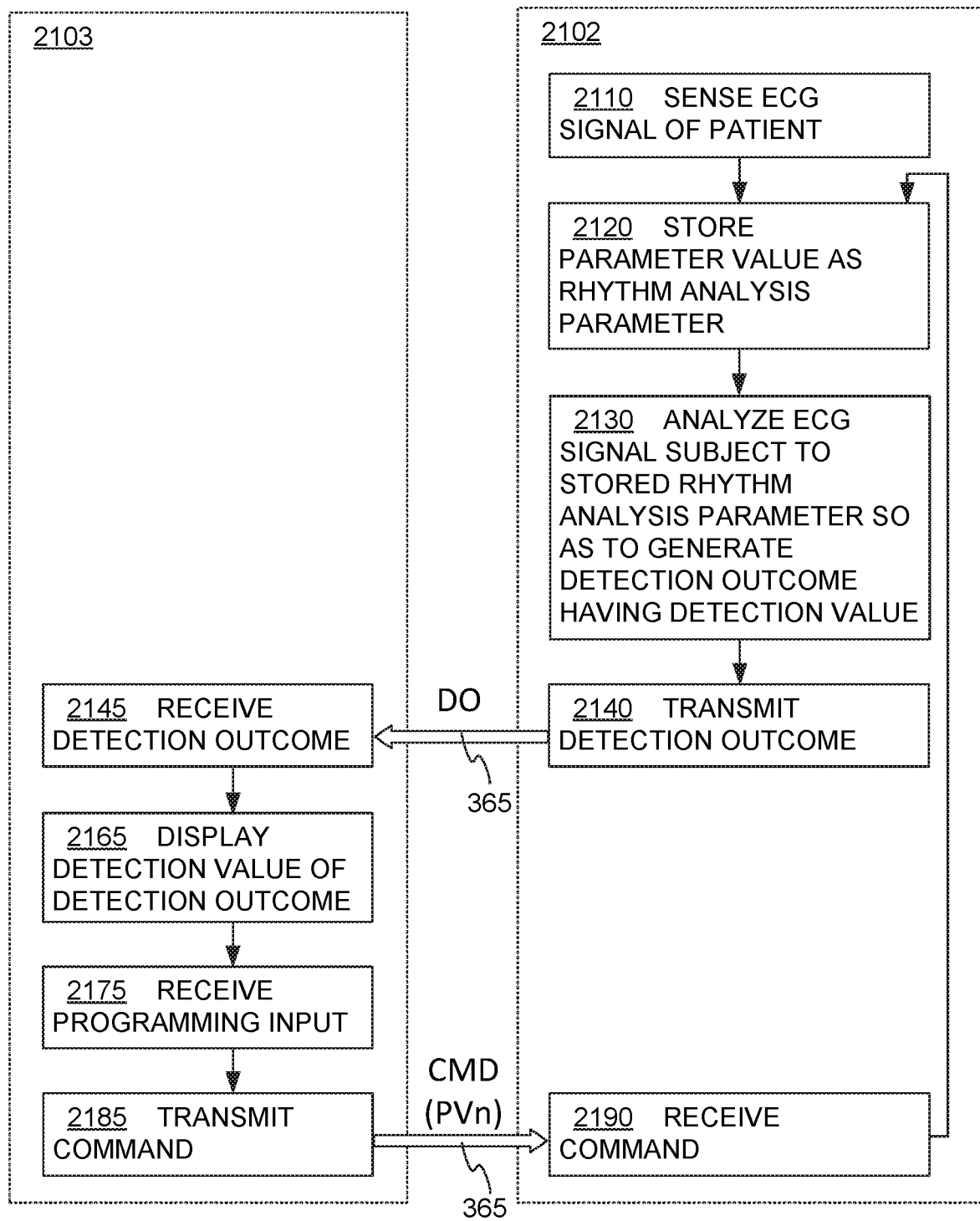
FIG. 21 is a diagram for illustrating more methods according to embodiments.

FIG. 21 shows flowcharts 2103, 2102 for describing methods according to embodiments. Flowchart 2103 is used for illustrating operations being performed by programming device 303 or 1703, while flowchart 2102 is used for illustrating operations being performed by wearable medical system 302 or 1702, which could be a WCD system. In combinations according to embodiments, operations from both flowcharts may be performed.

According to an operation 2110 of flowchart 2102, a parameter value may be stored in ambulatory memory 1738, as a rhythm analysis parameter. The first time operation 2110 is executed, a first parameter value PV1 may be stored.

According to another operation 2130, the sensed ECG signal may be analyzed subject to the parameter value that is stored as the rhythm analysis parameter, so as to generate a detection outcome DO from the sensed ECG signal. This analysis may be performed by ambulatory processor 1730. If first parameter value PV1 is stored, then the detection outcome DO may have a first detection value DV1 or DO(DV1).

According to another operation 2140, the detection outcome DO may be transmitted. Transmitting may be performed by an ambulatory communication module of a wearable medical system, over local communication link 365.

According to another operation 2145 of flowchart 2103, the detection outcome DO transmitted at operation 2140 may be received by a programming communication module, over local communication link 365.

According to another operation 2165, the received detection outcome may be displayed for the person to view, and in particular for viewing its detection value. Displaying may be performed by programming screen 1783. As also per the above, the parameter value that was used may also be displayed, along additional possible such parameter values. Moreover, a constructed version of the ECG signal may also be displayed, from ECG data that is further transmitted at operation 2140.

According to one more operation 2175, a programming input may be then received by the programming user interface. This programming input may have been entered by person 389, while viewing what was displayed per operation 2165. This programming input may be about the ambulatory processor transitioning to using a second parameter value PV2 instead of first parameter value PV1 as the rhythm analysis parameter, which is what person 389 may think can operate better for this particular patient.

According to an additional operation 2185, a command may be transmitted over local communication link 365, responsive to the programming input received at operation 2175. The command can be in furtherance of the programming input, for example about the ambulatory processor to transitioning to using the second parameter value PV2 as per the above.

According to another operation 2190 of flowchart 2102, the command transmitted at operation 2185 may be received by the ambulatory communication module. From operation 2190, execution may return to operation 2120. The second parameter value PV2 may be thus stored in ambulatory memory 1738 responsive to the command received at operation 2190. As such, second parameter value PV2 can then operate as the rhythm analysis parameter in lieu of first parameter value PV1.

Then operation 2130 may be repeated. Given the different rhythm analysis parameter value, a detection outcome DO may be generated that has a second detection value DV2 or DO(DV2), which is different than first detection value DO (DV1).

Then operations 2140, 2145, 2165 may be repeated, for the detection outcome with the second detection value.

Additional optional operations are possible, also from what was described above. For example, a rhythm statistic may be further extracted from the sensed ECG signal, for example by the ambulatory processor. This rhythm statistic can be transmitted and displayed.

Moreover, the detection outcome may be displayed as an event marker icon on the programming screen. The event marker icon may be further displayed at a place relative to the displayed ECG signal that indicates when the detection outcome was made relative to the ECG signal. Plus the programming user interface may receive from person 380 an activation input about the displayed event marker icon so as to further display determinative data, and so on. Event marker icons can be for instances as described above, and so on.

Figure 22:
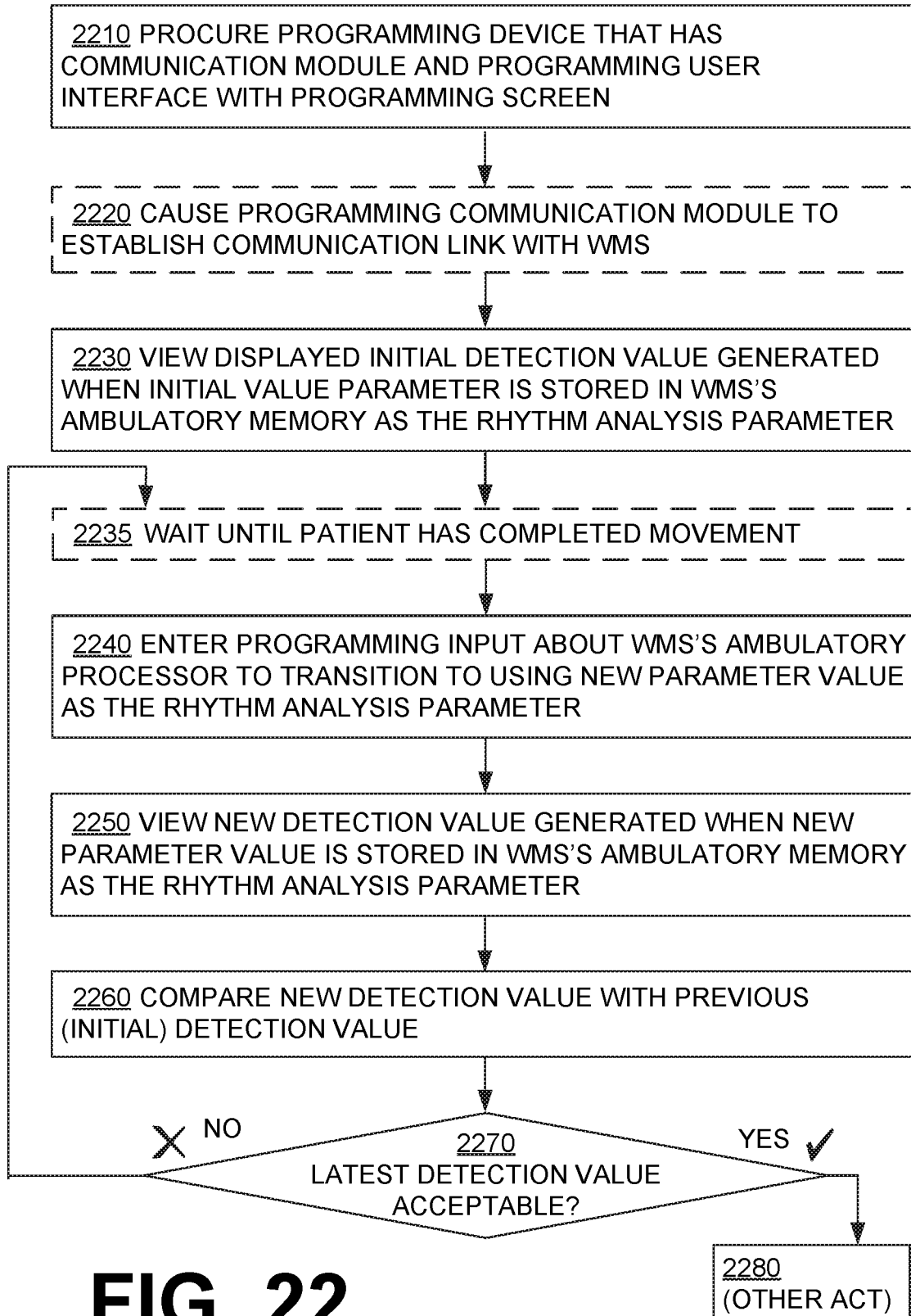
FIG. 22 is a flowchart for illustrating methods according to embodiments.

FIG. 22 shows a flowchart 2200 for describing methods according to embodiments, which can be performed by person 389 of FIG. 3. It will be appreciated that the methods of flowchart 2200 are methods of programming WMS 302, and not necessarily methods of directly administering treatment to patient 382.

According to an operation 2210, a programming device may be procured, such as programming device 303 and others described in this document.

According to another, optional operation 2220, a programming communication module of the procured programming device is caused to establish a communication link with the WMS. This may be performed automatically, or by actions of person 389.

According to another operation 2230, a displayed initial detection value may be viewed on a programming screen of the programming device. This initial detection value may be generated when an initial value parameter is stored in an ambulatory memory of the WMS as the rhythm analysis parameter. For instance, when operation 2230 is executed, a first detection value of the received detection outcome may be thus displayed, having been generated when a first value parameter is stored in the ambulatory memory as the rhythm analysis parameter.

According to another, optional operation 2235, person 389 may wait until the patient has completed a movement. The movement could be walking back and forth, a number of steps on a treadmill, another movement that person 389 has requested, and so on. An advantage of the programming being performed in an in-person session is that person 389 can personally ascertain what exactly movement patient 382 actually did. The movement may change physiological parameters of patient 382, such as elevate their heart rate, change their breathing, etc. Such a movement, and stopping of a movement, can provide more diverse data about patient 382, which person 382 can take into account for the programming operations. For example, person 389 may determine how much or how little walking on a treadmill results in the physiological parameters having returned to normal after 5 minutes, and so on. As such, person 389 can make adjustments in real time when testing/improving the algorithm, and while the WMS is subjected to real conditions, such as electrical noise from the electrodes, etc., so as to "narrow" down to optimal settings.

According to another operation 2240, a programming input may be entered by person 389 via a programming user interface of the programming device. The programming input can be about the ambulatory processor of the WMS transitioning to using a second parameter value instead of the first parameter value as the rhythm analysis parameter. When this happens, the programming communication module may transmit a command over the local communication link, the command in furtherance of the programming input. When this happens, the second parameter value may become stored in the ambulatory memory as the rhythm analysis parameter.

According to another operation 2250, a displayed second detection value of the received detection outcome may be viewed on the programming screen. This displayed second detection value can be generated when the second value parameter is stored in the ambulatory memory as the rhythm analysis parameter.

According to another operation 2260, the first and the second detection values may be compared—the second one still possibly displayed while the first one at least remembered.

According to another operation 2270, if the latest detection value is acceptable then programming for this parameter may be complete and, according to another operation 2280, other acts may be performed such as programming for another parameter. If not, then execution may return to operation 2235, where an additional movement may be waited for, an additional programming input can be entered, and so on, responsive to the comparison of operation 2270. The additional programming input can be about the ambulatory processor transitioning to using a third parameter value different from the second parameter value, and which can be the same as the first parameter value. Again, the programming communication module may transmit, responsive to the entered additional programming input, an additional command over the local communication link, in which the third parameter value becomes stored in lieu of the second parameter value in the ambulatory memory, and so on.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

The embodiments of the invention in which an exclusive property or privilege is claimed are defined as follows:

1. In combination, a wearable cardioverter defibrillator (WCD) system configured to be worn by an ambulatory patient and a programming device for a person other than the patient to program the WCD system, the WCD system comprising:
    a support structure configured to be worn by the ambulatory patient;
        electrodes coupled to the support structure, at least some of the electrodes configured to sense an electrocardiogram (ECG) signal of the patient;
        a defibrillator including an ambulatory processor, the ambulatory processor configured to analyze the sensed ECG signal so as to generate a detection outcome from the sensed ECG signal, the defibrillator configured to discharge, through the patient via at least some of the electrodes, an electrical charge responsive to the detection outcome having a particular value while the support structure is worn by the patient so as to deliver a shock to the patient, the defibrillator further including an ambulatory memory, the ambulatory processor configured to store in the ambulatory memory first ECG data about a first portion of the ECG signal and then, after a buffer period, to erase the first ECG data from the ambulatory memory by storing second ECG data over the first ECG data in the ambulatory memory, the second ECG data about a second portion of the ECG signal that is sensed subsequently to the first portion; and
        an ambulatory communication module coupled to at least one of the support structure and the defibrillator, the ambulatory communication module configured to transmit the first ECG data over a local communication link that is shorter than 99 feet in length, and
    the programming device distinct from the defibrillator and operable while not coupled to the support structure, the programming device comprising:
        a programming communication module configured to receive the transmitted first ECG data over the local communication link;
        a programming memory; and
        a programming processor configured to cause the programming memory to store the received first ECG data for a time at least twice as long as the buffer period.

2. The combination of claim 1, in which the local communication link is at least partially established by a cable.

3. The combination of claim 1, in which the local communication link is wireless.

4. The combination of claim 1, in which the programming device further comprises:
    a programming screen configured to display, after the first ECG data has been thus erased from the ambulatory memory, an image of the first portion of the ECG signal that is constructed from the received first ECG data.

5. The combination of claim 1, in which the ambulatory processor is configured to store in the ambulatory memory the second ECG data for a time longer than the buffer period, responsive to the detection outcome having a certain value.

6. The combination of claim 5, in which the ambulatory memory comprises a buffer portion and a long-term portion and the ambulatory processor is configured to store the first ECG data in the buffer portion and to store the second ECG data in the long-term portion.

7. The combination of claim 5, in which the ambulatory processor is configured to continuously store subsequent ECG data after the second ECG data is stored in the ambulatory memory.

8. The combination of claim 1, in which the ambulatory processor is configured to program an algorithm to store in the ambulatory memory the second ECG data for a time longer than the buffer period, responsive to the detection outcome having a certain value.

9. A method for a combination of a wearable cardioverter defibrillator (WCD) system configured to be worn by an ambulatory patient and a programming device for a person other than the patient to program the WCD system, the WCD system comprising a support structure worn by the ambulatory patient, electrodes coupled to the support structure, a defibrillator including an ambulatory processor and an ambulatory memory, an ambulatory communication module, a programming communication module and a programming memory, the programming device distinct from the defibrillator and operable while not coupled to the support structure, the programming device comprising a programming communication module, and a programming memory, the method comprising:
    sensing, via at least some of the electrodes, an electrocardiogram (ECG) signal of the patient;
    storing, in the ambulatory memory, first ECG data about a first portion of the ECG signal;
    analyzing, by the ambulatory processor, the sensed ECG signal so as to generate a detection outcome from the sensed ECG signal;
    then, after a buffer period, erasing the first ECG data from the ambulatory memory by storing second ECG data over the first ECG data in the ambulatory memory, the second ECG data about a second portion of the ECG signal that is sensed subsequently to the first portion;
    transmitting, by the ambulatory communication module, the first ECG data over a local communication link that is shorter than 99 feet in length;
    receiving, by the programming communication module over the local communication link, the transmitted first ECG data; and
    storing in the programming memory the received first ECG data for a time at least twice as long as the buffer period.

10. The method of claim 9, in which the local communication link is at least partially established by a cable.

11. The method of claim 9, in which the local communication link is wireless.

12. The method of claim 9, in which the programming device further comprises:
    a programming screen, and the method further comprises:
        displaying, after the first ECG data has been thus erased from the ambulatory memory, on the programming screen an image of the first portion of the ECG signal that is constructed from the received first ECG data.

13. The method of claim 9, in which the second ECG data is stored in the ambulatory memory for a time longer than the buffer period, responsive to the detection outcome having a certain value.

14. The method of claim 13, further comprising:
    discharging, by the defibrillator responsive to the detection outcome having a particular value, an electrical charge through at least some of the electrodes while the support structure is worn by the patient so as to deliver a shock to the patient.

15. The method of claim 14, in which the ambulatory memory comprises a buffer portion and a long-term portion and the ambulatory processor is configured to store the first ECG data in the buffer portion and to store the second ECG data in the long-term portion.

16. The method of claim 14, further comprising:
continuously storing subsequent ECG data after the second ECG data in the ambulatory memory.

17. The method of claim 9, further comprising:
programming an algorithm to store in the ambulatory memory the second ECG data for a time longer than the buffer period, responsive to the detection outcome having a certain value.

18. In combination, a wearable medical system (WMS) and a programming device, the WMS comprising:
a support structure configured to be worn by the ambulatory patient;
electrodes coupled to the support structure, at least some of the electrodes configured to sense an electrocardiogram (ECG) signal of the patient;
a defibrillator including an ambulatory processor, the ambulatory processor configured to analyze the sensed ECG signal so as to generate a detection outcome from the sensed ECG signal, the defibrillator configured to discharge, through the patient via at least some of the electrodes, an electrical charge responsive to the detection outcome having a particular value while the support structure is worn by the patient so as to deliver a shock to the patient, the defibrillator further including an ambulatory memory, the ambulatory processor configured to store in the ambulatory memory first ECG data about a first portion of the ECG signal and then, after a buffer period, to erase the first ECG data from the ambulatory memory by storing second ECG data over the first ECG data in the ambulatory memory, the second ECG data about a second portion of the ECG signal that is sensed subsequently to the first portion, the ambulatory processor further configured to store in the ambulatory memory the second ECG data for a time longer than the buffer period, responsive to the detection outcome having a certain value; and
an ambulatory communication module coupled to at least one of the support structure and the defibrillator, the ambulatory communication module configured to transmit the first ECG data over a local communication link that is shorter than 99 feet in length, and
the programming device distinct from the defibrillator and operable while not coupled to the support structure, the programming device comprising:
a programming communication module configured to receive the transmitted first ECG data over the local communication link;
a programming memory; and
a programming processor configured to cause the programming memory to store the received first ECG data for a time at least twice as long as the buffer period.

19. The combination of claim 18, in which the ambulatory processor is configured to continuously store subsequent ECG data after the second ECG data in the ambulatory memory.

20. The combination of claim 18, in which the ambulatory processor is configured to program an algorithm to store in the ambulatory memory the second ECG data for a time longer than the buffer period, responsive to the detection outcome having a certain value.

* * * * *